(12) United States Patent
Janda

(10) Patent No.: US 11,660,331 B2
(45) Date of Patent: May 30, 2023

(54) HEROIN VACCINE

(71) Applicant: THE SCRIPPS RESEARCH INSTITUTE, La Jolla, CA (US)

(72) Inventor: Kim D. Janda, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 219 days.

(21) Appl. No.: 16/761,012

(22) PCT Filed: Nov. 8, 2018

(86) PCT No.: PCT/US2018/059724
§ 371 (c)(1),
(2) Date: May 1, 2020

(87) PCT Pub. No.: WO2019/094528
PCT Pub. Date: May 16, 2019

(65) Prior Publication Data
US 2021/0268088 A1 Sep. 2, 2021

Related U.S. Application Data

(60) Provisional application No. 62/583,637, filed on Nov. 9, 2017.

(51) Int. Cl.
*A61K 39/00* (2006.01)
*A61K 47/64* (2017.01)
(Continued)

(52) U.S. Cl.
CPC ............ *A61K 39/0013* (2013.01); *A61K 9/19* (2013.01); *A61K 39/39* (2013.01); *A61K 47/26* (2013.01);
(Continued)

(58) Field of Classification Search
None
See application file for complete search history.

(56) References Cited

U.S. PATENT DOCUMENTS

| 5,610,283 A | 3/1997 | Beuchler |
| 6,262,265 B1 | 7/2001 | Rouhani et al. |

(Continued)

FOREIGN PATENT DOCUMENTS

| WO | 2004/111202 A2 | 12/2004 |
| WO | 2013/095321 A1 | 6/2013 |

(Continued)

OTHER PUBLICATIONS

Bremer PT, Schlosburg JE, Banks ML, Steele FF, Zhou B, Poklis JL, Janda KD. Development of a Clinically Viable Heroin Vaccine. J Am Chern Soc. Jun. 28, 2017;139(25):8601-8611. doi: 10.1021/jacs.7b03334. Epub Jun. 20, 2017. PMID: 28574716; PMCID: PMC5612493. (Year: 2017).*

(Continued)

*Primary Examiner* — Michelle S Horning
(74) *Attorney, Agent, or Firm* — Hugh Wang; Thomas Fitting; Edward Grieff

(57) ABSTRACT

An improved heroin conjugate vaccine is detailed; to accomplish this task the systematic exploration of twenty vaccine formulations with varying combinations of carrier proteins and adjuvants were undertaken. In regard to adjuvants, a Toll-like receptor 9 (TLR9) agonist and a TLR3 agonist in the presence of alum were explored. The vaccine formulations containing TLR3 or TLR9 agonist alone-elicited strong anti-heroin antibody titers and blockade of heroin-induced antinociception when formulated with alum; however, a combination of TLR3 and 9 adjuvants did not result in improved efficacy. Investigation of stability of the two lead formulations revealed that the TLR9 but not the TLR3 formulation was stable when stored over 30 days. Further- (Continued)

more, mice immunized with the TLR9+alum heroin vaccine gained significant protection from lethal heroin doses, suggesting that this vaccine formulation is suitable for mitigating the lethal effects of heroin, even following long-term storage at room temperature.

20 Claims, 6 Drawing Sheets

(51) Int. Cl.
  *A61K 47/54* (2017.01)
  *A61K 9/19* (2006.01)
  *A61K 39/39* (2006.01)
  *A61K 47/26* (2006.01)

(52) U.S. Cl.
  CPC ............ *A61K 47/54* (2017.08); *A61K 47/643* (2017.08); *A61K 47/646* (2017.08); *A61K 47/6415* (2017.08); *A61K 2039/55505* (2013.01); *A61K 2039/55561* (2013.01); *A61K 2039/6037* (2013.01); *A61K 2039/6081* (2013.01)

(56) References Cited

U.S. PATENT DOCUMENTS

| | | | |
|---|---|---|---|
| 8,357,375 | B2 | 1/2013 | Palma et al. |
| 2003/0170728 | A1 | 9/2003 | McConnell et al. |
| 2014/0093525 | A1 | 4/2014 | Pentel et al. |
| 2015/0343054 | A1 | 12/2015 | Janda |
| 2015/0374836 | A1 | 12/2015 | Portoghese et al. |
| 2016/0144023 | A1* | 5/2016 | Cui ................... A61K 9/14 424/490 |
| 2017/0266278 | A1 | 9/2017 | Gudkov et al. |

FOREIGN PATENT DOCUMENTS

| | | |
|---|---|---|
| WO | 2014/124317 A1 | 8/2014 |
| WO | 2017/023904 A3 | 2/2017 |
| WO | 2017/127390 A1 | 7/2017 |
| WO | 2018/080838 A1 | 5/2018 |

OTHER PUBLICATIONS

Bremer, et al., Conjugate Vaccine Immunotherapy for Substance Use Disorder, Pharmacological Reviews, Jul. 2017, Rev. 69, p. 298-315.

Bremer, et al., Angew Chem Int Ed Engl, Combatting Synthetic Designer Opioids: Active Vaccination Ablates Lethal Doses of Fentanyl Class Drugs, Mar. 7, 2016; 55(11), p. 3772-3775.

Bremer, et al., J. Med Chem, Investigating the Effects of a Hydrolytically Stable Hapten and a Th1 Adjuvant on Heroin Vaccine Performance, Dec. 13, 2012, 55(23), p. 10776-10780.

Bremer, et al., Molecular Pharmaceutics, Injection Route and TLR9 Agonist Addition Significanly Impact Heroin Vaccine Efficacy, 2014, 11, p. 1075-1080.

Brown, et al., Tetrahedron Letter, Synthesis of a Morphine-6-Glucuronide Hapten, N-(4-Aminobutyl)normorphine-6-Glucuronide, and Related Haptens, 1995 vol. 36, No. 47, p. 8661-8664.

CAS 1345833-61-5.

CAS 1345833-64-8.

Hwang, et al., Mol Pharm, Enhancing Efficacy and Stability of an antiheroin Vaccine: Examination of Antinociception, Opioid Binding Profile, and Lethality, Mar. 5, 2018, 15(3), p. 1062-1072.

\* cited by examiner

| Compound | Cross-Reactivity (%) |
|---|---|
| Oxycodone | 0.08 |
| Methadone | 0.07 |
| Buprenorphine | 0.08 |
| Norbuprenorphine | 0.08 |
| Naloxone | 0.10 |
| Naltrexone | 0.10 |
| Morphine | 0.10 |

HEROIN VACCINE

CROSS REFERENCE TO RELATED APPLICATIONS

This application is a U.S. national stage of International Patent Application No. PCT/US2018/059724 (filed Nov. 8, 2018; now pending); which claims benefit to U.S. Provisional Patent Application No. 62/583,637 (filed Nov. 9, 2017), each of which is incorporated by reference in its entirety.

STATEMENT OF GOVERNMENT SUPPORT

This invention was made with government support under grant number DA041146 awarded by the National Institutes of Health. The government has certain rights in the invention.

BACKGROUND

Heroin is a schedule I, highly addictive opioid drug and a significant public health concern. In the US, drug overdose deaths have nearly tripled between 1999 and 2014.[1] In 2015, 52,404 overdose deaths were reported, 63% of which involved opioids.[1] Recently, there has been a marked increase in prescriptions of synthetic opioid pain relievers (OPRs) for management of chronic pain.[2] Evidence suggests that misuse of OPRs is the strongest risk factor for initiating heroin abuse, and OPR users are 40 times more likely to abuse heroin.[3,4] This phenomenon is driven by the relatively low cost of heroin and its wide availability.[3,4] Current treatments for heroin addiction involve opioid replacement therapy e.g., methadone administration, to promote heroin detoxification.[5] Unfortunately, the addictive nature of heroin and other opioids, combined with the adverse effects of withdrawal and high cost of treatment, lead to a high incidence of drug relapse.[5,3,4] In the face of increasing opioid abuse and overdose, the development of improved therapies that can attenuate the effects of opioids is crucial.

Vaccination is a promising strategy to promote cessation of heroin abuse and prevent relapse. Implementation of this strategy involves active immunization using a small molecule-protein conjugate, which elicits high-affinity, drug-specific antibodies. These polyclonal IgG antibodies sequester free drug in the blood and prevent access to the brain, subsequently reducing the drug compound's psychoactive effects. This approach has been pre-clinically validated for vaccines against nicotine,[6,7] cocaine,[8,9] and methamphetamine.[10,11] For heroin specifically, vaccination efficacy has been repeatedly demonstrated in mice, rats, and non-human primates.[12-15]

In general, formulation of a vaccine with an adjuvant is an attractive approach to enhance the magnitude and length of vaccine immunity against the target antigen by stimulating antigen presenting cells, T-cells or B-cells. Historically, alum has been the most commonly used adjuvant, but numerous alternatives have been pursued in recent years.[16] Adjuvants can act as pathogen-associated molecular patterns (PAMPs), which activate Toll-like receptors (TLRs) resulting in upregulation of an immune response. Specific PAMPs include lipopolysaccharides (LPS), double-stranded RNA (dsRNA) and unmethylated cytosine-guanine (CpG) motifs.[16] However, at this time only a limited number of adjuvants are approved for use in humans. By exploring new adjuvants or combinations of adjuvants, we can rationally design vaccines with enhanced immunogenicity directed toward production of heroin-neutralizing antibodies. CpG oligodeoxynucleotide (ODN) 1826 is a B-class ODN that stimulates B-cell responses though TLR9[17,18] and was recently shown to elicit robust titers in anti-heroin vaccine studies.[13,19] Natural or synthetic dsRNA, e.g., polyinosiic:polycytidylic acid (poly 1:C), is a molecular pattern associated with viral replication, which elicits an immune response via TLR3 and has been used as an effective adjuvant in several vaccine studies.[20-22] Given the potent immunostimulatory capacity of viral or bacterial PAMPs, we were interested in evaluating the efficacy of a yeast-derived viral dsRNA genome relative to CpG ODN, using a well-studied dsRNA virus of *Saccharomyces cerevisiae*, L-A.[23] To date, only the L-BC viral dsRNA genome generated from infected *S. cerevisiae* has been used as an adjuvant, where it increased immunogenicity of a prophylactic viral vaccine in mice.[24]

SUMMARY

In recent years, drug conjugate vaccines have shown promise as therapeutics for substance use disorder. As a means to improve the efficacy of a heroin conjugate vaccine, we systematically explored twenty vaccine formulations with varying combinations of carrier proteins and adjuvants. In regard to adjuvants, we explored a Toll-like receptor 9 (TLR9) agonist and a TLR3 agonist in the presence of alum. The TLR9 agonist was cytosine-guanine oligodeoxynucleotide 1826 (CpG ODN 1826), while the TLR3 agonist was virus-derived genomic doubled-stranded RNA (dsRNA). The vaccine formulations containing TLR3 or TLR9 agonist alone elicited strong anti-heroin antibody titers and blockade of heroin-induced antinociception when formulated with alum; however, a combination of TLR3 and 9 adjuvants did not result in improved efficacy. Investigation of long-term stability of the two lead formulations revealed that the TLR9 but not the TLR3 formulation was stable when stored as a lyophilized solid or as a liquid over 30 days. Furthermore, mice immunized with the TLR9+alum heroin vaccine gained significant protection from lethal heroin doses, suggesting that this vaccine formulation is suitable for mitigating the harmful effects of heroin, even following long-term storage at room temperature.

DETAILED DESCRIPTION

Here, we investigate L-A-derived dsRNA in combination with alum and/or CpG ODN in the context of our drug of abuse vaccine. Although alum is not necessary for TLR activation, it is one of the few FDA-approved adjuvants and has shown promising activity in anti-drug vaccines. In comparison to alum, we selected conjugatable adjuvant lipid vesicles (CALV) as an alternative vehicle for vaccine delivery.[25] CALVs are nanoparticulate liposomes designed to effectively deliver encapsulated antigens for immune uptake.

Figure 1:
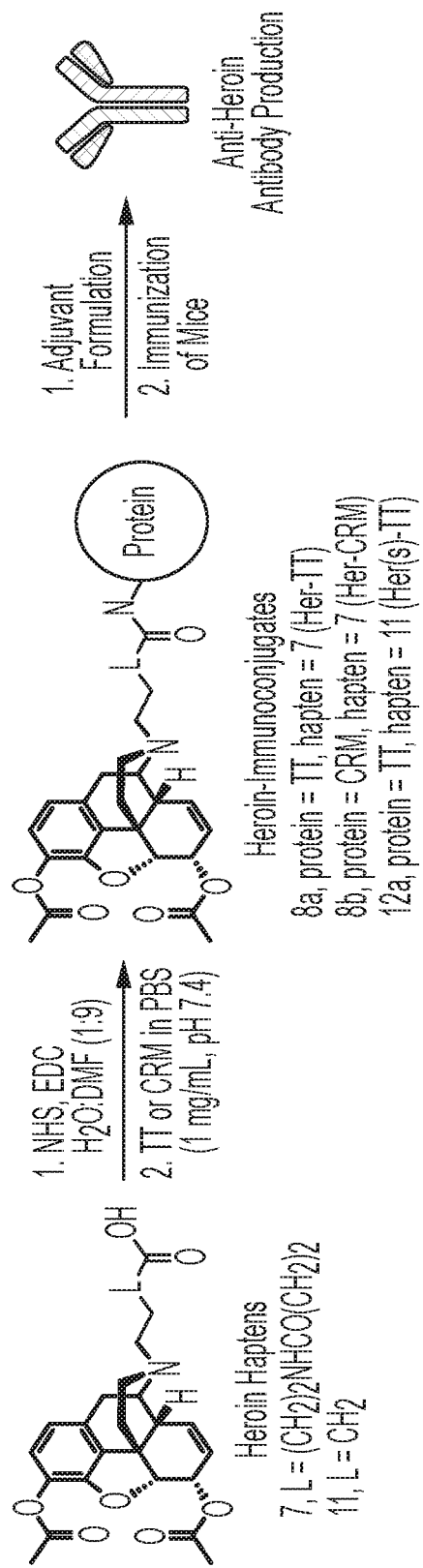
FIG. 1. Structures of the heroin haptens, corresponding immunoconjugates and the general vaccine approach. The structure of heroin is highlighted in red.

Our most successful anti-heroin vaccine to date involves a second generation heroin hapten adjuvanted with alum and CpG (FIG. 1).[19] We used this formulation as a benchmark while investigating new adjuvant combinations and formulation conditions in an effort to find a lead vaccine candidate. We then measured the effects of adjuvant dosing on vaccine efficacy, and the vaccines were tested under various storage conditions for stability as a liquid or lyophilized solid after mixing with alum adjuvant and trehalose as a cryoprotectant. Our most successful formulation was then selected for an overdose challenge to see if protection was conferred against a lethal dose of heroin.

Synthesis of Heroin Haptens and Conjugation to Carrier Proteins

The synthesis and characterization of the heroin haptens and immunoconjugates are described in detail in the Examples, along with additional information on animals, formulation conditions, vaccine administration schedule, behavioral testing, ELISA and other experimental data. Our key hapten design element is a strategically placed linker on the nitrogen that ultimately presents an immune epitope with high structural congruence to heroin. (7, FIG. 1, Examples, Scheme 1).[19] We also prepared a heroin hapten with a truncated linker at this same position to probe the effect of linker length on vaccine efficacy (11, FIG. 1). The haptens were activated and conjugated to carrier protein tetanus toxoid (TT) or a mutant diphtheria toxoid (CRM), using an EDC-mediated coupling reaction (FIG. 1), followed by dialysis against pH 7.4 phosphate buffered saline (PBS). The degree of haptenation was determined by MALDI-ToF mass spectrometry, using a heroin-bovine serum albumin (Her-BSA) immunoconjugate as a surrogate for determining hapten density. Immunoconjugates were stored at −80° C. until the day of formulation and vaccination.

Vaccine Formulation

After conjugation of the proteins, immunoconjugates were formulated with different adjuvants as described in Tables S1-5. The adjuvants were CpG ODN 1826, dsRNA, Alhydrogel (alum), and VesiVax® CALV.[25] CpG ODN 1826 is a phosphorothioated oligonucleotide with the following sequence (5' to 3'): TCCATGACGTTCCTGACGTT (SEQ ID NO: 1). The 4.6 kb viral dsRNA was derived from L-A infected *S. cerevisiae* (ATCC #22244). The VesiVax® CALV liposomes and dsRNA were obtained from Molecular Express, Inc. Each vaccine was prepared by shaking the mixture for twenty minutes prior to injection. The delivered dose of each component was 200 μg immunoconjugate, 50 μg of CpG ODN 1826 or dsRNA, and 1 mg of alum per animal for each injection, unless noted otherwise in Table 1 and Tables S1-5.

All animals in a given series were run at the same time, except for Series D and G. The bold lines separating the series indicate that the series were run in two sets, instead of simultaneously (Table S2 and S5). Mice were bled on day 38 using retro-orbital puncture in order to collect approximately 100-150 μL of whole blood, unless noted otherwise. Groups were composed of 4 to 6 mice. Mice were group-housed in an AAALAC-accredited vivarium containing temperature and humidity controlled rooms, and kept on a reverse light cycle (lights on: 9 PM-9 AM). Immunoconjugate 12a with the shortened linker hapten was used in Group B4 and the hapten 11 was termed H(s) in Table 1 and S1.

Antinociception Assays

On week 6, antinociceptive responses under escalating heroin doses were evaluated to determine vaccine-mediated blockade of heroin psychoactivity.[26] A set of mice was tested for spinal (tail immersion) and supraspinal (hot plate) antinociceptive responses to thermal stimuli at 54° C., according to our laboratory procedure.[27] Following administration of the drug, the analgesic effect (represented as maximal possible effect, % MPE) was measured for each test after every dose. The data were then fit using a non-linear regression in GraphPad PRISM to determine $ED_{50}$ values.

ELISAs

Bleeds were taken on weeks 6 and 10 for Series B, and maximum titer levels occurred at week 6. Therefore, we opted to perform bleeds on day 38 for Series C-G, and perform antinociception assays around week 6. Since heroin is rapidly metabolized to 6-AM before entering the brain,[28,29] an ELISA using heroin or 6-monoacetylmorphine (6-AM) as coating antigens was performed for Series E to characterize antigen specificity of the antibody response. The equivalent titer response to coating antigen may suggest that the heroin immunoconjugate hydrolyzes to 6-AM before or during antigen presentation.

Analyzing Cross-Reactivity of Polyclonal Anti-Heroin Antibodies by Surface Plasmon Resonance The binding $IC_{50}$ for mouse serum IgGs from Group G6 and 6-AM was determined by competitive binding assay via surface plasmon resonance (SPR) using a Biacore 3000 instrument (GE Healthcare) equipped with a research-grade CM5 sensor chip according to literature methods.[30] Diluted mouse serum from day 38 was incubated with serial dilutions of heroin, 6-AM, methadone, oxycodone, naloxone, buprenorphine, norbuprenorphine, naltrexone and morphine and injected into a Biacore 3000 containing a Her-BSA-loaded sensor chip. The heroin-BSA conjugate, was immobilized on the sensor chip using a NHS, EDC-mediated coupling reaction. The conjugate was resuspended in 10 mM sodium acetate (pH 4.0) was immobilized at a density of 5,000 RU on flow cell 2; whereas flow cell 1 was immobilized with BSA at the same density to serve as a reference surface. All the surfaces were blocked with a 7 min injection of 1.0 M ethanolamine-HCl (pH 8.5). The pooled mouse sera was diluted in running buffer (HBS-EP+buffer) and titrated on both coated flow cells, so as to give a response of ~100 RU within 3 minutes of injection and 2.5 minute dissociation at a flow rate of 30 μL/min. The chip surface was regenerated by injection of 10 mM Gly-HCl (pH 1.5) for 30 seconds before the next round of assays. Signal produced by antibody binding to the SPR chip without drug present was used as a reference for 100% binding.

Statistical Analysis

Tests for homogeneity of variance and normal distribution were performed on behavioral observation test scores. If conditions were met, analyses of variance (ANOVAs) were performed. Results were analyzed via one-way ANOVA with Dunnett's post hoc comparisons for titers and Tukey's post hoc test for analgesia. Pearson correlation coefficient was used to test the linear relationship between anti-heroin midpoint titers to analgesia results for all animals tested (hot plate, P=0.002, $R^2$=0.093, tail immersion, P=0.009, $R^2$=0.047).

Results and Discussion

Series A-C: Preliminary Evaluation of dsRNA as an Adjuvant

To evaluate the series of heroin vaccine formulations, mice (n=4-6/group) were vaccinated subcutaneously (s.c.) with the specific formulations listed in Tables S1-5. Series A through C were designed to broadly explore the scope of vaccine conditions with the new dsRNA adjuvant in multiple contexts and to compare the adjuvant to our most successful heroin vaccine: Her-TT adjuvanted with 50 ug CpG adjuvanted and 1 mg of alum (Group A6). We used our previously reported second-generation heroin hapten[17] in the majority of our formulations, (7, FIG. 1) although a truncated heroin hapten (11, FIG. 1), was compared to 7 and showed no difference in behavioral efficacy (Group B4, Table 1). Moreover, ELISA results revealed that antibody titers for both hapten 7 and 11 vaccination groups were similar regardless of coating antigens (8c and 12b), suggesting that the hapten linker does not noticeably affect immunogenicity or antibody-hapten binding. In moving forward with hapten 7, optimization of vaccine formulation conditions for the dsRNA included varying the carrier protein, the delivery system (i.e., CALV liposomal delivery or alum as a depot), and combining CpG and dsRNA. Findings from the first three series (highlighted in red in Table 1) were used to guide successive series of refinement. The subsequent Series D and E were designed to focus on a specific TLR agonist and observe its response to dose ranging with alum. After establishing an optimal dose with each TLR agonist, the integrity of the vaccine was tested under various storage conditions (Series F and G).

Following behavioral assays and titer measurements of all the series, a one-way ANOVA was performed on the resulting data (Table 1). The ANOVA confirmed a significant effect of formulation conditions in the hot plate assay [F (37, 135)=5.851; p<0.001]. A similar result was observed for the ANOVA in the tail flick assay [F (37,135)=22.92; p<0.001]. A Dunnett or Tukey post hoc test was then used to confirm significance among the groups. In Series A-C, we observed several interesting trends pertaining to (1) RNA vs. DNA-based adjuvants, (2) carrier protein, (3) delivery vehicle, and (4) preliminary vaccine stability (FIG. 2).

Figure 2A:
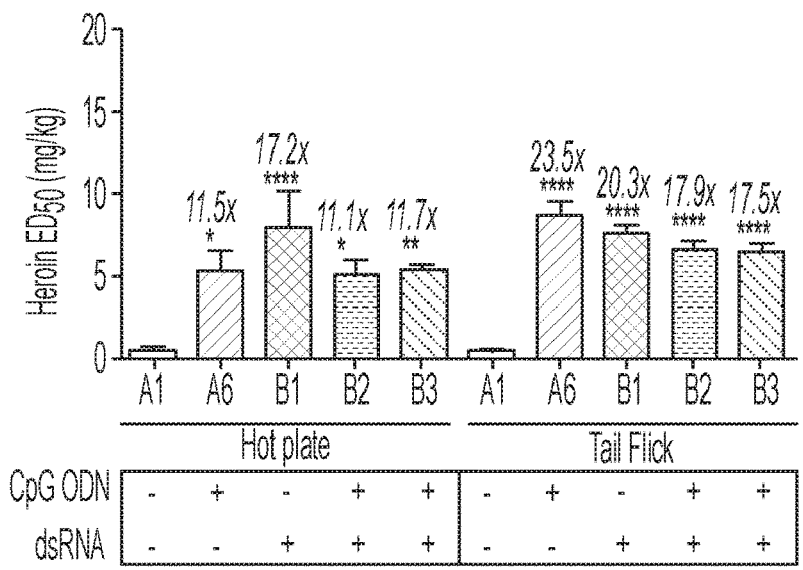
FIG. 2. Effects of adjuvants and carrier proteins on heroin vaccine efficacy in antinociception assays. Panel A shows the effects of RNA vs. DNA, Panel B shows the effect of carrier protein, Panel C displays the effect of alum versus CALV as delivery vehicles. Italicized numbers above the bars represent the $ED_{50}$ ratio vs. nonvaccinated control animals from control A1. A one-way ANOVA was performed for each antinociception assay, followed by a Dunnett's post hoc comparison test, respectively. *$P<0.05$, $P<0.01$, **$P<0.0001$ versus control A1.

Comparison of CpG and dsRNA as adjuvants revealed equipotency in the context of TT as the carrier protein co-administered with alum (FIG. 2A). Intriguingly, the addition of CpG to the dsRNA/TT/alum formulation did not improve efficacy (Group B2, FIG. 2A), indicating that the adjuvants do not act synergistically and possibly interfere with each other's adjuvant effects.

Figure 2B:
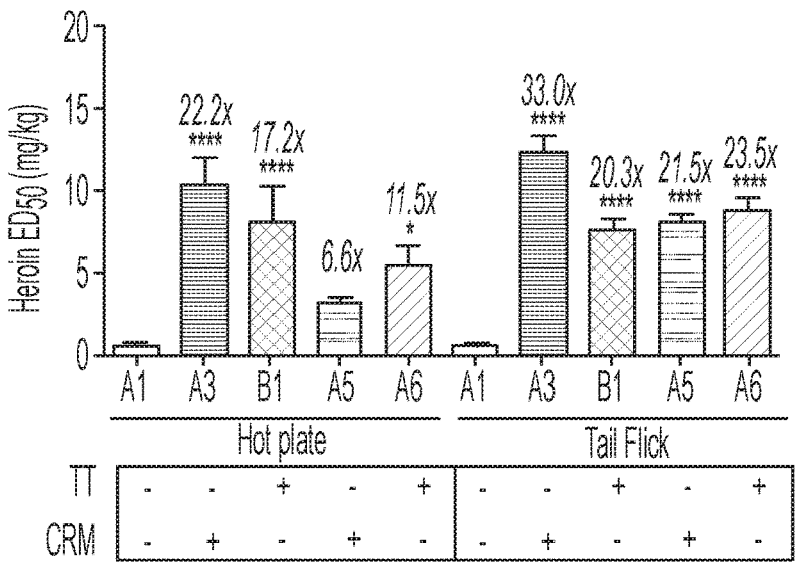

When a non-toxic mutant of diphtheria toxin, CRM, was employed as a carrier in eliciting an immunogenic response, we found that CRM adjuvanted with dsRNA was superior in both antinociception assays, as compared to TT (p<0.001, FIG. 2B). However despite this increased efficacy, we opted to perform the rest of the vaccine studies with TT due to the fact that the CRM conjugate had an unfortunate tendency to precipitate upon storage.

Figure 2C:
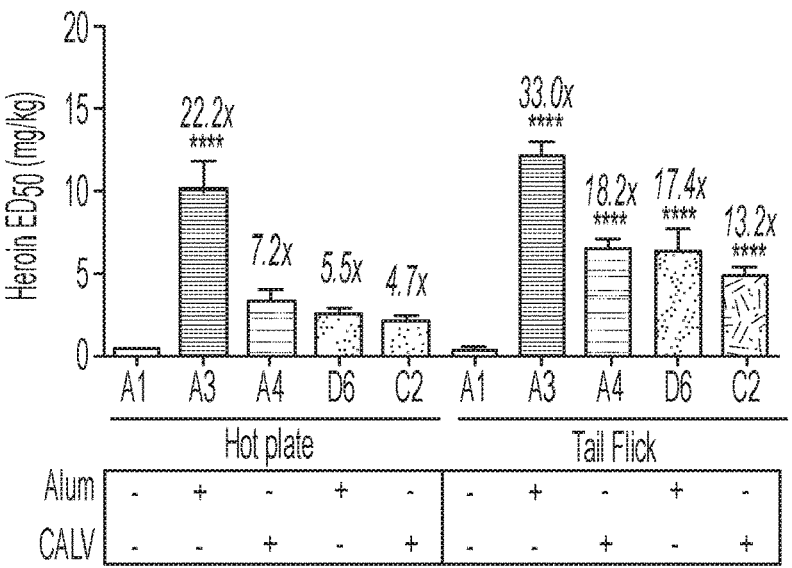

In comparing CALV liposomes and alum, anti-heroin antibody titers were higher in alum formulations than liposomal formulations. Moreover, CALV formulations (Groups A4, C1-C3 FIG. 2, Table 1) were not as effective as vaccines containing alum in protecting mice from heroin-induced antinociception (FIG. 2C, Table 1). A notable difference in efficacy was observed when CRM was adjuvanted with alum versus CALV liposomes, although this trend was not observed for TT. It is possible that the large disparity between the two delivery conditions may be due to the marked aggregation of Her-CRM during conjugation, which would impede subsequent encapsulation by liposomes. On the other hand, Her-TT's solubility would theoretically permit encapsulation by CALV liposomes, possibly explaining the fact that CALV Her-TT liposomes gave the same magnitude of protection against heroin compared to Her-TT adjuvanted with a low dose of alum (0.2 mg/dose). Based on the finding that CALV was moderately effective as a Her-TT adjuvant, but never superior to alum, we did not move forward with CALV in our DNA and RNA dose-ranging studies.

Series D and E: RNA and DNA Adjuvant Dose-Ranging with Alum

In any vaccine, the beneficial immunopotentiation of adjuvants needs to be balanced against the risk of adverse side effects. Unfortunately, potent adjuvant action is often correlated with increased toxicity, presenting as inflammation at the site of immunization. Even FDA approved adjuvants like alum are known to produce inflammation at the injection site.[31, 32] Preliminary assessment of toxicities in Series A-C showed occasional injection site redness and swelling, particularly in formulations containing dsRNA. Although injection site reactions are typical with alum-containing vaccines, we hypothesized that refining adjuvant dosing parameters might reduce the incidence and severity of these reactions.

Figure 3A:
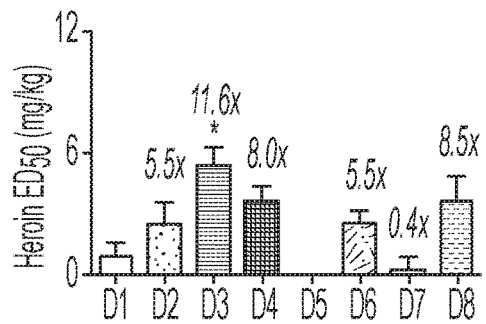
FIG. 3. Dose-ranging effects of dsRNA or CpG with alum on vaccine efficacy. Panels A and E are hot plate antinociceptive tests, Panels B and F are tail immersion tests, Panels C and G are anti-heroin midpoint titers and D and H are injection site reactions measured on the day of antinociception. Italicized numbers above the bars represent the $ED_{50}$ ratio vs. nonvaccinated control animals from control A1. A one-way ANOVA was performed for each antinociception assay and the titer data, followed by a Dunnett's or Tukey's post hoc comparison test, respectively. *P<0.05, P<0.01, **P<0.0001 versus control A1. #P<0.0001 versus control C1.
Figure 3B:
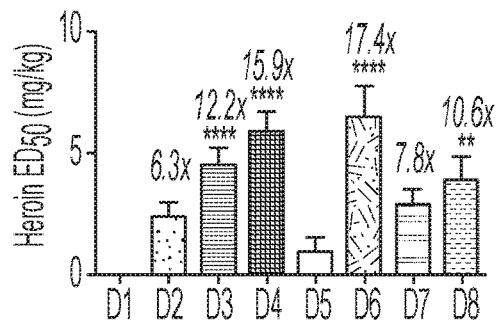
Figure 3C:
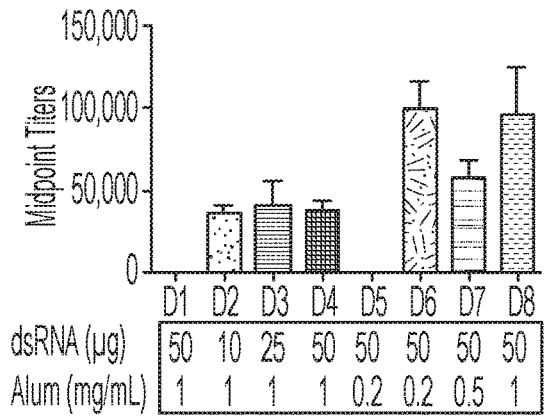
Figure 3D:
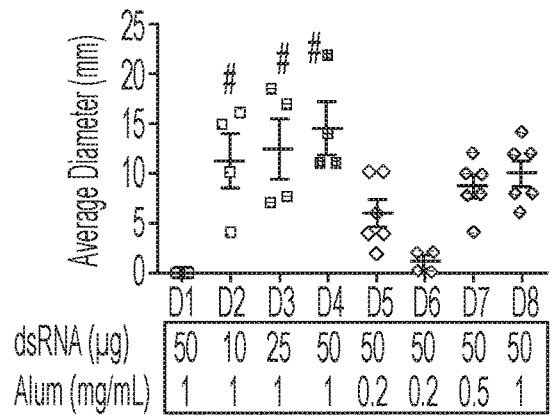
Figure 3E:
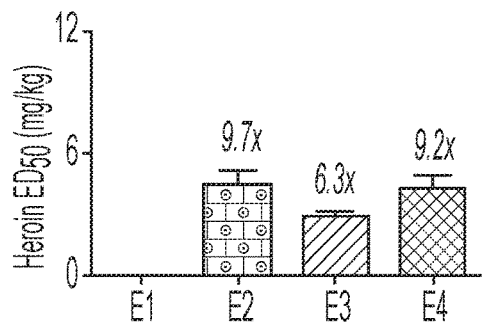
Figure 3F:
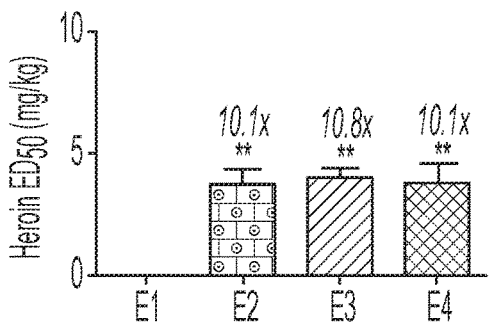

Initial screenings of candidate formulations suggested that the preparations containing both dsRNA and alum yielded superb antibody and antinociceptive responses (Table 1). We specifically investigated different dsRNA to alum ratios in the mouse antinociception models to further refine the vaccine formulation. We hypothesized that at lower doses of alum and/or dsRNA, we might be able to lessen the severity of the injection site reactions without an appreciable loss of immunogenicity. Increasing the amount of dsRNA in vaccine formulations with 1 mg of alum (Groups D2-D4, Table 1) increased the size and/or incidence of injection site reactions. The increased inflammatory effect was also reflected in an increase in vaccine efficacy in the tail immersion response, but not in hot plate antinociception test (FIGS. 3A and B). However, we found that lower doses of alum (0.2 mg) dramatically reduced the injection site reactions without compromising the efficacy of the vaccine for the dsRNA series (FIGS. 3A, B and D). In terms of the CpG series, we found that decreasing the alum had no effect on efficacy and that CpG formulations with the lowest alum dose were still adequately efficacious (FIG. 3E-F). CpG dosing was previously reported and demonstrated a positive correlation between vaccine efficacy and CpG dose with no increase in adverse reactions.[19]

Series F and G: Stability of Vaccines Under Various Storage Conditions and Time Periods Another important goal in vaccine design is achieving long-term shelf stability without loss in efficacy, typically via lyophilization; consequently, protection of the vaccine components against damage during the freezing and drying process is essential.[33] Trehalose can be used as an effective cryoprotectant to prevent alum aggregation during lyophilization,[34, 35] therefore we investigated the stability and efficacy of our heroin vaccines under various storage conditions in the presence of trehalose. In a preliminary study, we tested a lyophilized vaccine formulation containing 15% w/v trehalose as a cryoprotectant (Group B3, Table 1). When immunized with the reconstituted vaccine, this group demonstrated similar efficacy to the non-lyophilized vaccine Group B2 in antinociceptive assays (FIG. 2A, Table 1). This initial result prompted us to explore a broader range of conditions for each nucleotide-based adjuvant and their relative shelf stability over time. For both the dsRNA and CpG series, Her-TT immunoconjugate was formulated with trehalose and dsRNA or CpG, samples were initially stored in the −80° C. freezer, defrosted, mixed with alum and then subjected to the following storage conditions (Figure S16): (1) formulated with alum one day before injection and stored as a liquid at 4° C. (Groups F1 and G1); (2) formulated with alum thirty days before injection and stored as a liquid at 4° C. (Groups F2 and G2) or stored at room temperature (RT, Group G6); (3) formulated with alum one day before injection, lyophilized, and stored at RT (Groups F3, G3, and G7); (5) formulated with alum thirty days before injection, lyophilized, and stored at RT (Groups F4, G4, and G8, Table 1). As a negative control in the CpG series, Groups G1-G4, Table 1 were spiked with a lower amount of trehalose (>5%) to measure its effect on protection from lyophilization. On the day of injection, all lyophilized samples were resuspended in water via twenty minutes of vortex mixing, then administered to mice.

Figure 3G:
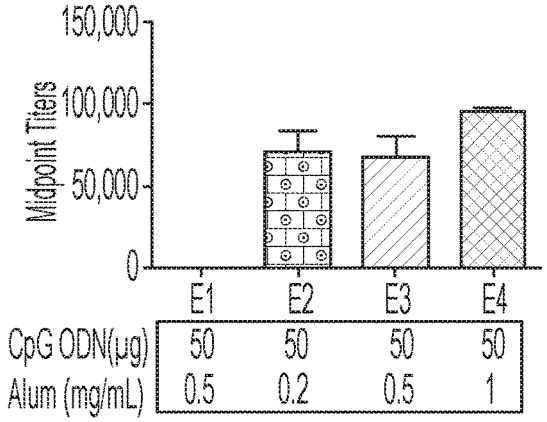
Figure 3H:
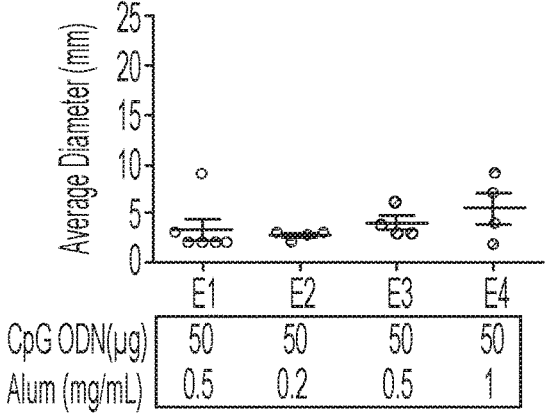
Figure 4A:
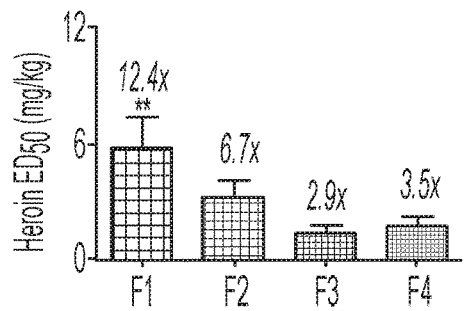
FIG. 4. The stability of dsRNA+alum (A-D) and CpG+alum (E-H) vaccines under liquid and solid storage conditions over time. Panels A and E are hot plate antinociceptive tests, Panels B and F are tail immersion tests, Panels C and G are anti-heroin midpoint titers and D and H are injection site reactions measured the day of antinociception. Italicized numbers above the bars represent the $ED_{50}$ ratio vs. non-vaccinated control animals from control A1. In the legend, L and S stand for liquid or solid, respectively. A one-way ANOVA was performed for each antinociception assay and the titer data, followed by a Dunnett's or Tukey's post hoc comparison test, respectively. *P<0.05, P<0.01, *P<0.001****P<0.0001 versus control A1. #P<0.01 Tukey's comparison test for titer between G4 and G8, which differed only in percentage of trehalose added.
Figure 4B:
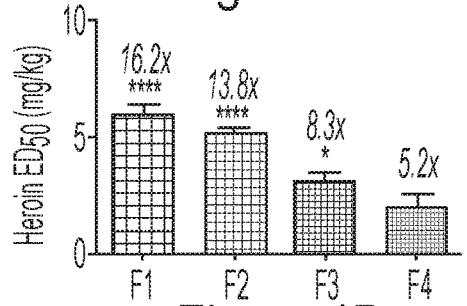
Figure 4C:
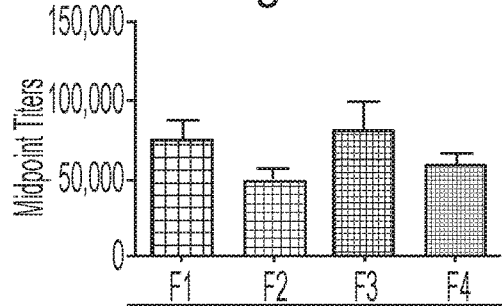
Figure 4D:
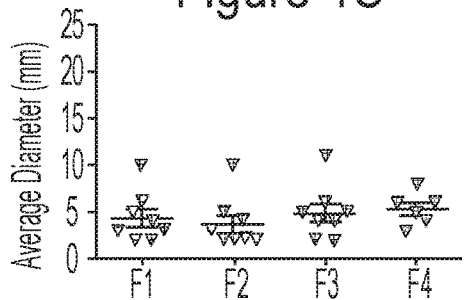
Figure 4E:
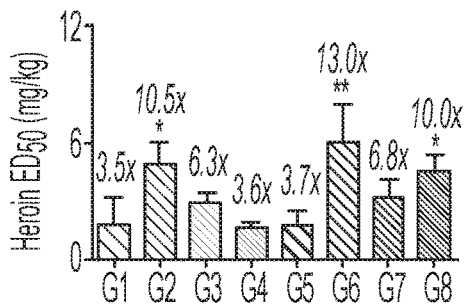
Figure 4F:
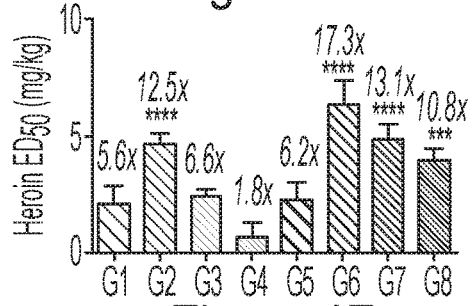
Figure 4G:
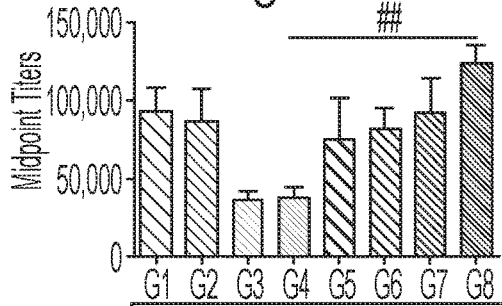
Figure 4H:
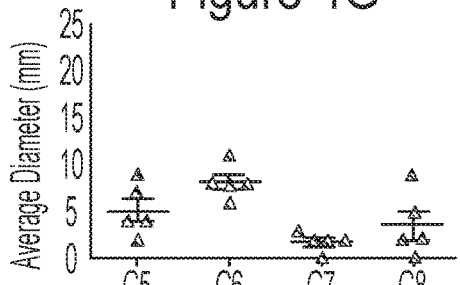

In interpreting the dsRNA series results, lyophilized vaccines (Groups F3 and F4) were not as effective in tail immersion and hot plate thermal nociception as compared to liquid storage for one day (Group F1, FIGS. 4A and B, Table 1). Samples stored for thirty days also showed modestly lower titer levels (Groups F2 and F4, FIG. 4C, Table 1). These results could be explained by the possible instability of the dsRNA genome at room temperature, as cold storage (−20 to −80° C.) is optimal for most extracted DNA samples.[36] On the other hand, extended incubation and storage apparently enhanced efficacy for the CpG series (G Series, FIG. 4E-H), possibly due to the formation of immunologically active antigen-alum aggregates during storage.[37] In assessing the effects of the cryoprotectant, liquid samples with CpG were effective regardless of the presence of trehalose over time (Group G2); however, lyophilized samples without at least 15% trehalose do not survive under storage conditions after thirty days as evidenced by reduced in vivo efficacy (Group G4, FIG. 3E-G, Table 1). When a sufficient amount of trehalose was used in the vaccine formulations, lyophilized vaccines performed better at both one and thirty-day time points in thermal nociception assays and titer (G3 vs. G7 for one day, G4 vs. G8 for thirty day lyophilized, FIG. 4E-G, Table 1). Promisingly, the efficacy of the vaccine was retained after 30 days as a liquid (G2 and G6) or when lyophilized (G8), and there was no significant difference between the samples that were lyophilized thirty days or one day prior to injection (G8 and G7, respectively, Table 1).

Figure 5A:
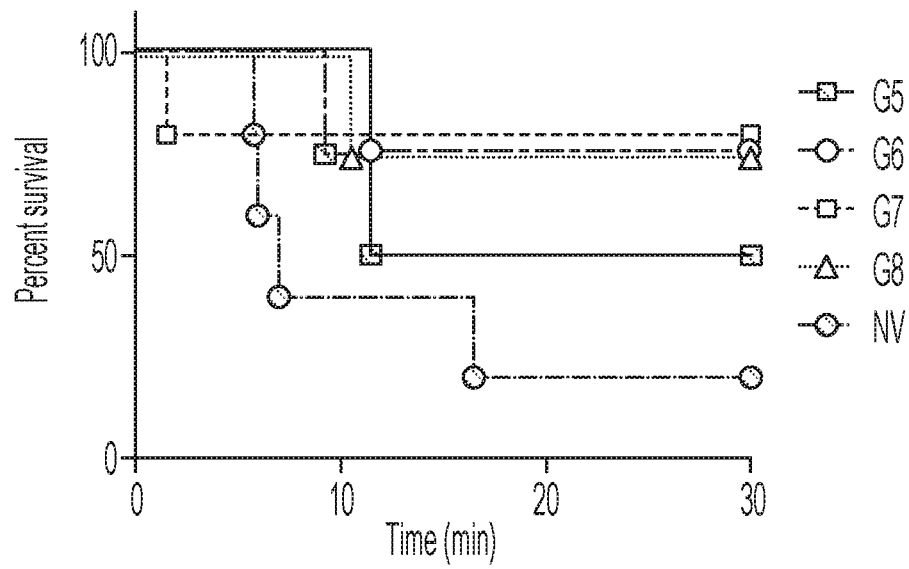
FIG. 5. Efficacy of heroin vaccine against a lethal heroin challenge. Panel A shows the survival curve of each vaccinated treatment group and nonvaccinated (NV, n=5) mice challenged with a 160 mg/kg dose (i.p.) and observed for thirty minutes. Panel B shows the vaccinated mice (n=13) from the groups that demonstrated efficacious vaccine potency in comparison to the control (n=5). Panel C shows the vaccinated mice that did not meet our efficacy cutoff criterion (n=4, G5) versus the nonvaccinated mice (n=5). Nonvaccinated mice were given a 2 mg/kg dose of heroin the same day the vaccinated mice underwent antinociception assays. The lethal challenge was performed the following week. A nonparametric, unpaired Mann-Whitney U test was performed and revealed survival between the two groups were statistically significant (P<0.05). Bars represent mean survival percentage±SEM.
Figure 5B:
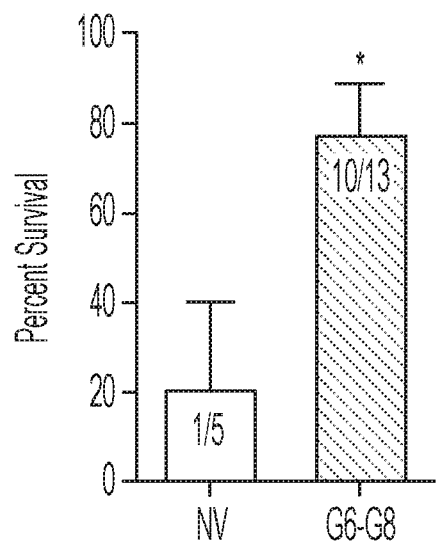
Figure 5C:
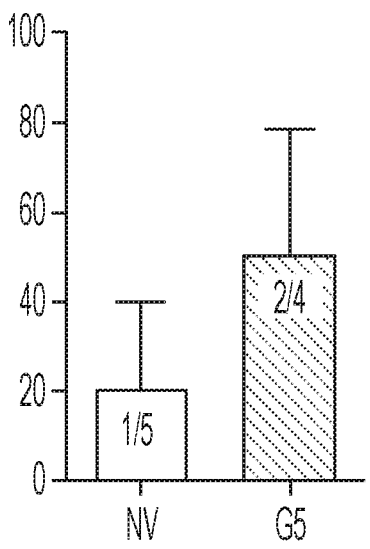

Upon demonstrating that our vaccine could block substantial doses of heroin in the antinociception assay, we examined the ability of our vaccine to mitigate heroin-induced lethality. Based on the antinociceptive data for the stability studies, we defined an efficacious vaccine as a vaccine group having an $ED_{50} \geq 4.5$ mg/kg in at least one measure of thermal nociception. Using this criterion, the CpG series with 25% cryoprotectant were the most successful. Thus, vaccinated mice (n=17) from the CpG stability studies and nonvaccinated mice (n=5) were administered a 160 mg/kg dose of heroin and survival was measured (FIG. 5A). The survival rate for the pooled efficacious vaccine group was 77% (10 of 13 mice survived), as compared to 20% survival for the nonvaccinated (1 of 5 mice survived, FIG. 5B). Taken together, these results clearly indicate that the heroin vaccine is highly effective in diminishing the effects of a lethal heroin challenge in rodents.

Cross-Reactivity of Antibodies from Group G6

Figures 6A, 6B:
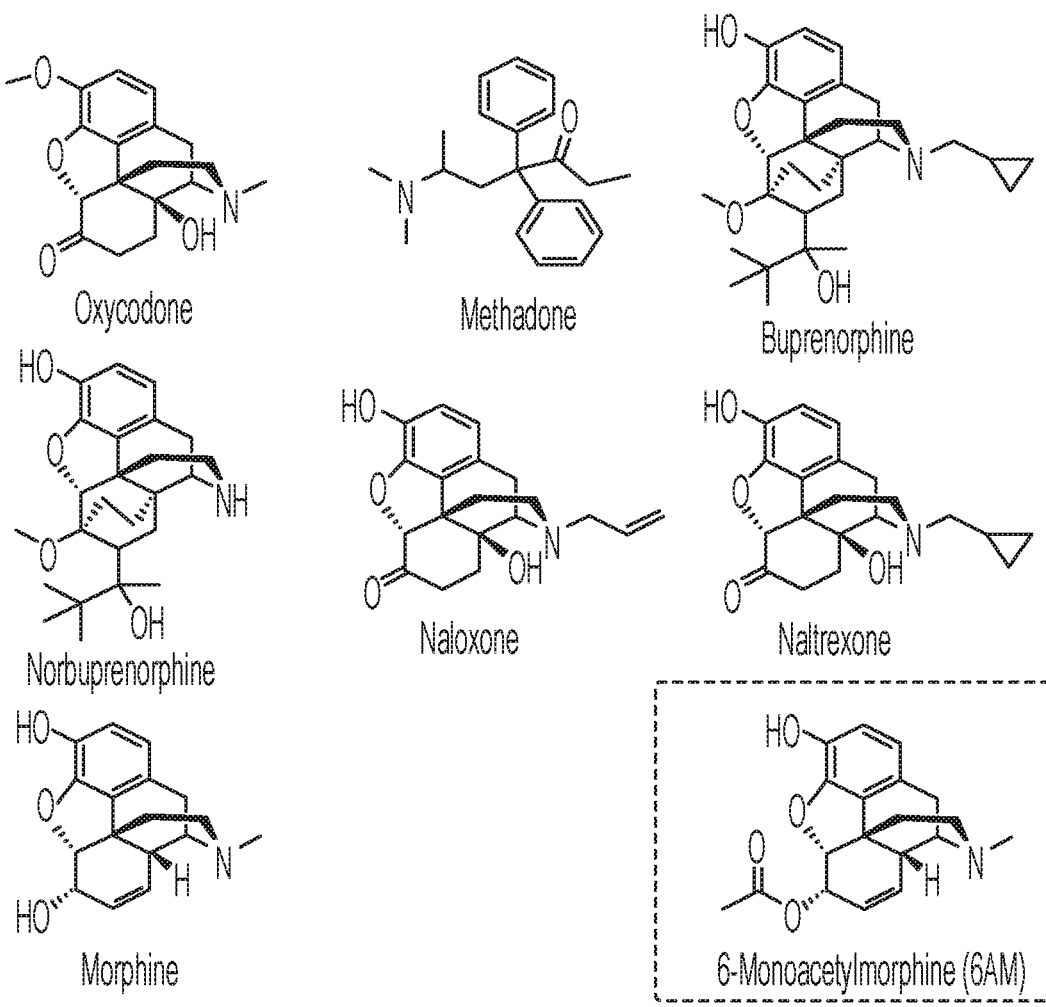
FIG. 6. Cross-reactivity of anti-heroin polyclonal antibodies from Group G6 to other therapeutic opioids as determined by surface plasmon resonance (SPR) binding assay. Panel A contains the structures of the relevant opioids. Panel B shows the cross-reactivity of therapeutic opioids (10 μM) compared to 6-AM on a Her-BSA-loaded sensor chip incubated with diluted mouse sera from G6. Surface plasmon resonance revealed the $IC_{50}$ value of 6-AM for Group G6 was ~100 nM. The $IC_{50}$ value of heroin could not be determined by SPR due to the rapid hydrolysis of heroin to 6-AM during experimental runs.

A major benefit of vaccination over traditional pharmacotherapies stems from the increased duration of action of circulating antibodies and decreased side effects. The advancement of a heroin vaccine may benefit from a combination therapy with existing drugs, such as methadone or burprenorphine, to mitigate opioid cravings during cessation therapy. To test whether combination therapy was feasible with our heroin vaccine, we selected Group G6 (Table 1) from the stability series and characterized the polyclonal antibody response by SPR. Sera from Group G6 were pooled to measure the binding affinities of polyclonal antibodies in vaccinated mouse serum G6 for heroin, 6-AM, and morphine using a Biacore 3000 equipped with a Her-BSA-coated chip. Diluted mouse sera was then preincubated with serial dilutions of FDA-approved therapeutic opioids (FIG. 6A) to test for potential cross-reactivity that might interfere with combination therapy.

Using the SPR competition assay, it was determined that the polyclonal antibodies from G6 had a binding affinity for 6-AM corresponding to ~100 nM. Interestingly, even though the formulation parameters for G6 was storage as a liquid at room temperature, the low cross-reactivity of morphine to the polyclonal antibodies suggests minimal 6-AM hydrolysis over 30 days in phosphate buffered saline (pH 7.4) with trehalose (25% w/v). In addition, it was demonstrated that affinities for FDA-approved opioids were >1,000 times lower compared to 6-AM (FIG. 6B), indicating minimal cross-reactivity to therapeutic opioids. These data suggest that Her-TT vaccinated subjects may use pharmacotherapies in tandem with vaccination.

We have examined adjuvant formulation and carrier protein in the context of our heroin vaccine in order to improve vaccine efficacy. Substituting CRM197 for TT as a carrier protein gave similar efficacy in heroin antinociception tests. Evaluation of an RNA-based adjuvant similar to TLR3 agonist poly(I:C), showed an increase in vaccine efficacy versus our previously used TLR9 adjuvant, CpG, while a combination of the two was not as effective. Furthermore, formulation of the RNA adjuvant without alum or with a liposome (CALV) showed poor vaccine efficacy. Dosing of the adjuvants with alum and dsRNA or CpG was optimized to reduce injection site reactions while maintaining vaccine efficacy. The RNA-based adjuvant in combination with a lower dose of alum was promising, while CpG was unaffected by alum dosing, so both RNA and DNA adjuvant vaccines were further explored in stability studies.

In the dsRNA stability studies, it was determined that vaccines containing dsRNA perform the best one day after formulation. Liquid dsRNA and CpG samples stored for thirty days at 4° C. were comparable, but the CpG vaccine stored as a liquid at RT surpassed both adjuvant samples in the measures of vaccine efficacy. In terms of lyophilized treatment, trehalose is essential for lyophilized vaccine performance. Both lyophilized CpG samples with 25% trehalose (w/v) achieved much higher $ED_{50}$'s than the lyophilized dsRNA samples. Therefore for our lethality challenge, we tested the CpG stability series and found that the vaccine conferred protection against a lethal dose of heroin. Based on the results of this systematic formulation assessment for vaccines against heroin abuse, the CpG+alum Her-TT formulation has demonstrated the most promise to move beyond preclinical development.

TABLE 1

Summary of vaccine formulations and results. First section (A, B, C) indicates the adjuvant selection studies, the second section (D, E) indicates the adjuvant and alum dosing; the third section (F, G) indicates the stability studies.

| Group | Vaccine | Immuno-conjugate (μg/dose)[a] | Alum (mg/dose)[a] | Adjuvant (mg/dose)[a] | Cryo-protectant (w/v or v/v)[b] | Mice (/group) | Hot Plate (ED$_{50}$) | Tail Flick (ED$_{50}$) | Midpoint Titers[d] (×10³) |
|---|---|---|---|---|---|---|---|---|---|
| A1 | vehicle | — | 1 | — | glycerol | 6 | 0.5 ± 0.1[e] | 0.4 ± 0.1[e] | n.d.[f] |
| A2 | H-CRM-RNA | 50 μg Her-CRM | — | 50 μg dsRNA | glycerol | 4 | 0.6 ± 0.5 | 6.8 ± 0.5 | 6 ± 1 |
| A3 | H-CRM-Alum-RNA | 50 μg Her-CRM | 1 | 50 μg dsRNA | glycerol | 4 | 10.2 ± 1.7 | 12.2 ± 0.9 | 21 ± 5 |
| A4 | H-CRM-CALV-RNA | 50 μg Her-CRM | — | 2.5 mg CALV + 50 μg dsRNA | glycerol | 4 | 3.3 ± 0.8 | 6.7 ± 0.5 | 4 ± 2 |
| A5 | H-CRM-Alum-CpG | 50 μg Her-CRM | 1 | 50 μg CpG | glycerol | 4 | 3.0 ± 0.5 | 8.0 ± 0.3 | 19 ± 3 |
| A6 | H-TT-Alum-CpG | 50 μg Her-TT | 1 | 50 μg CpG | glycerol | 4 | 5.3 ± 1.2 | 8.7 ± 0.8 | 18 ± 10 |
| B1 | H-TT-Alum-RNA | 50 μg Her-TT | 1 | 50 μg dsRNA | glycerol | 4 | 7.9 ± 2.3 | 7.5 ± 0.5 | 28 ± 3 |
| B2 | H-TT-Alum-CpG + RNA | 50 μg Her-TT | 1 | 50 μg CpG + 50 μg dsRNA | glycerol | 4 | 5.1 ± 0.8 | 6.6 ± 0.4 | 55 ± 8 |
| B3 | H-TT-Alum-CpG + RNA-Lyo | 50 μg Her-TT | 1 | 50 μg CpG + 50 μg dsRNA | 15% trehalose | 6 | 5.4 ± 0.3 | 6.5 ± 0.4 | 46 ± 4 |
| B4 | H(s)-TT-Alum-CpG | 50 μg Her(s)-TT | 1 | 50 μg CpG | glycerol | 4 | 5.7 ± 0.7 | 9.6 ± 0.4 | 44 ± 2 |
| B5 | (IP) H-TT-Aum-CAG | 50 μg Her-TT | 1 | 50 μg CpG | glycerol | 4 | 9.6 ± 1.5 | 13.4 ± 1.2 | 103 ± 30 |
| C1 | H-TT-Alum-RNA-CALV | 50 μg Her-TT | 0.2 | 2.5 mg CALV + 50 μg dsRNA | glycerol | 5 | 2.9 ± 0.8 | 3.2 ± 0.6 | 68 ± 9 |
| C2 | H-TT-RNA-CALV | 50 μg Her-TT | — | 2.5 mg CALV + 50 μg dsRNA | glycerol | 5 | 2.2 ± 0.3 | 4.9 ± 0.5 | 28 ± 4 |
| C3 | H-TT-CALV | 50 μg Her-TT | — | 2.5 mg CALV | glycerol | 5 | 1.0 ± 1.5 | 2.5 ± 0.6 | 15 ± 5 |
| D1 | KLH (vehicle) | 50 μg Her-TT | 1 | 50 μg dsRNA | glycerol | 4 | 0.9 ± 0.7[e] | 0.0 ± 0.0[e] | n.d.[f] |
| D2 | H-TT-Alum-RNA(L) | 50 μg Her-TT | 1 | 10 μg dsRNA | glycerol | 4 | 2.5 ± 1.1 | 2.3 ± 0.6 | 36 ± 5 |
| D3 | H-TT-Alum-RNA(M) | 50 μg Her-TT | 1 | 25 μg dsRNA | glycerol | 4 | 5.4 ± 0.9 | 4.5 ± 0.7 | 42 ± 13 |
| D4 | H-TT-Alum-RNA(H) | 50 μg Her-TT | 1 | 50 μg dsRNA | glycerol | 4 | 3.7 ± 0.7 | 5.9 ± 0.8 | 38 ± 6 |
| D5 | KLH (vehicle) | 50 μg KLH | 0.2 | 50 μg dsRNA | glycerol | 4 | 0.0 ± 0.0[e] | 1.0 ± 0.6[e] | n.d.[f] |
| D6 | H-TT-Alum(L)-RNA | 50 μg Her-TT | 0.2 | 50 μg dsRNA | glycerol | 4 | 2.6 ± 0.5 | 6.4 ± 1.3 | 99 ± 17 |
| D7 | H-TT-Alum(M)-RNA | 50 μg Her-TT | 0.5 | 50 μg dsRNA | glycerol | 4 | 0.2 ± 0.7 | 2.9 ± 0.6 | 57 ± 11 |
| D8 | H-TT-Alum(H)-RNA | 50 μg Her-TT | 1 | 50 μg dsRNA | glycerol | 4 | 3.7 ± 1.2 | 3.9 ± 0.9 | 96 ± 29 |
| E1 | KLH (vehicle) | 50 μg KLH | 0.5 | 50 μg CpG | — | 4 | 0.0 ± 0.0[e] | 0.0 ± 0.0[e] | n.d.[f] |
| E2 | H-TT-Alum(L)-CpG | 50 μg Her-TT | 0.2 | 50 μg CpG | — | 4 | 4.5 ± 0.7 | 3.7 ± 0.6 | 71 ± 12 |
| E3 | H-TT-Alum(M)-CpG | 50 μg Her-TT | 0.5 | 50 μg CpG | — | 4 | 2.9 ± 0.3 | 4.0 ± 0.3 | 67 ± 12 |
| E4 | H-TT-Alum(H)-CpG | 50 μg Her-TT | 1 | 50 μg CpG | — | 4 | 4.2 ± 0.6 | 3.8 ± 0.8 | 94 ± 3 |
| F1 | H-TT-Alum-RNA (1 d) | 50 μg Her-TT | 0.2 | 50 μg dsRNA | 25% trehalose | 5 | 5.7 ± 1.7 | 6.0 ± 0.5 | 75 ± 13 |
| F2 | H-TT-Alum-RNA (30 d) | 50 μg Her-TT | 0.2 | 50 μg dsRNA | 25% trehalose | 5 | 3.1 ± 0.9 | 5.1 ± 0.3 | 49 ± 8 |
| F3 | H-TT-Alum-RNA-Lyo | 50 μg Her-TT | 0.2 | 50 μg dsRNA | 25% trehalose | 5 | 1.3 ± 0.4 | 3.1 ± 0.4 | 81 ± 19 |
| F4 | H-TT-Alum-RNA-Lyo (30 d) | 50 μg Her-TT | 0.2 | 50 μg dsRNA | 25% trehalose | 5 | 1.6 ± 0.6 | 1.9 ± 0.6 | 59 ± 7 |
| G1 | H-TT-Alum-CpG (1 d, 4° C.) | 50 μg KLH | 1 | 50 μg CpG | >5% trehalose | 5 | 1.7 ± 1.5 | 2.1 ± 0.8 | 93 ± 16 |

TABLE 1-continued

Summary of vaccine formulations and results. First section (A, B, C) indicates the adjuvant selection studies, the second section (D, E) indicates the adjuvant and alum dosing; the third section (F, G) indicates the stability studies.

| Group | Vaccine | Immuno-conjugate (μg/dose)[a] | Alum (mg/dose)[a] | Adjuvant (mg/dose)[a] | Cryo-protectant (w/v or v/v)[b] | Mice (/group) | Hot Plate (ED$_{50}$) | Tail Flick (ED$_{50}$) | Midpoint Titers[d] (×10$^3$) |
|---|---|---|---|---|---|---|---|---|---|
| G2 | H-TT-Alum-CpG (30 d, 4° C.) | 50 μg Her-TT | 1 | 50 μg CpG | >5% trehalose | 5 | 4.8 ± 1.3 | 4.6 ± 0.6 | 86 ± 21 |
| G3 | H-TT-Alum-CpG-Lyo | 50 μg Her-TT | 1 | 50 μg CpG | >5% trehalose | 5 | 2.9 ± 0.6 | 2.4 ± 0.3 | 37 ± 4 |
| G4 | H-TT-Alum-CpG-Lyo (30 d) | 50 μg Her-TT | 1 | 50 μg CpG | >5% trehalose | 5 | 1.6 ± 0.3 | 0.7 ± 0.6 | 39 ± 6 |
| G5 | H-TT-Alum-CpG (0 d) | 50 μg Her-TT | 1 | 50 μg CpG | 25% trehalose | 5 | 1.7 ± 0.8 | 2.3 ± 0.7 | 75 ± 26 |

Antinociception Assay[c]

TABLE S1

Series A: initial screening of formulations; Series B: optimization of vaccine candidate formulations; Series C: delivery with lipsome versus alum

| Group | Vaccine | HerCRM/HerTT (μg/dose) | Alum (mg/mL) | Adjuvant | Route | Vaccination Schedule (days) | Bleeds (days) | Behavioral Assay (days) | Mice |
|---|---|---|---|---|---|---|---|---|---|
| A1 | vehicle | — | 1 | — | s.c./s.c./s.c. | 0, 14, 28 | 42 | 45 | 6 |
| A2 | H-CRM-RNA | 50 μg Her-CRM | — | 50 μg dSRNA | s.c./s.c./s.c. | 0, 14, 28 | 42 | 45 | 4 |
| A3 | H-CRM-Alum-RNA | 50 μg Her-CRM | 1 | 50 μg dSRNA | s.c./s.c./s.c. | 0, 14, 28 | 42 | 45 | 4 |
| A4 | H-CRM-CALV-RNA | 50 μg Her-CRM | — | 2.5 mg CALV + 50 μg dSRNA | s.c./s.c./s.c. | 0, 14, 28 | 42 | 45 | 4 |
| A5 | H-CRM-Alum-CpG | 50 μg Her-CRM | 1 | 50 μg CpG | s.c./s.c./s.c. | 0, 14, 28 | 42 | 45 | 4 |
| A6 | H-TT-Alum-CpG | 50 μg Her-TT | 1 | 50 μg CpG | s.c./s.c./s.c. | 0, 14, 28 | 42 | 45 | 4 |
| B1 | H-TT-Alum-RNA | 50 μg Her-TT | 1 | 50 μg dSRNA | s.c./s.c./s.c. | 0, 14, 28 | 42, 70 | 47 | 4 |
| B2 | H-TT-Alum-CpG + RNA | 50 μg Her-TT | 1 | 50 μg CpG + 50 μg dSRNA | s.c./s.c./s.c. | 0, 14, 28 | 42, 70 | 47 | 4 |
| B3 | H-TT-Alum-CPG + RNA-Lyo (Lyophilized and reconstituted) | 50 μg Her-TT | 1 | 50 μg CpG + 50 μg dSRNA | s.c./s.c./s.c. | 0, 14, 28 | 42, 70 | 47 | 6 |
| B4 | H(s)-TT-Alum-CpG (i.e.. short heroin hapten) | 50 μg Her-TT | 1 | 50 μg CpG | s.c./s.c./s.c. | 0, 14, 28 | 42, 70 | 47 | 4 |
| B5 | (IP) H-TT-Alum-CpG | 50 μg Her-TT | 1 | 50 μg CpG | i.p./i.p/i.p. | 0, 14, 28 | 42, 70 | 47 | 4 |
| C1 | H-TT-Alum-RNA-CALV | 50 μg Her-TT | 0.2 | 2.5 mg CALV + 50 μg dSRNA | s.c./s.c./s.c. | 0, 14, 28 | 38 | 42 | 5 |
| C2 | H-TT-RNA-CALV | 50 μg Her-TT | — | 2.5 mg CALV + 50 μg dSRNA | s.c./s.c./s.c. | 0, 14, 28 | 38 | 42 | 5 |
| C3 | H-TT-CALV | 50 μg Her-TT | — | 2.5 mg CALV | s.c./s.c./s.c. | 0, 14, 28 | 38 | 42 | 5 | s.c., subcutaneous;
i.p., intraperitoneal;
H(s), stands for the shorter hapten 11

TABLE S2

Series D: Dose ranging dsRNA; alum ratio study design

| Group | Vaccine | HerTT (μg/dose) | Alum (mg/mL) | Adjuvant | Route | Vaccination Schedule (days) | Bleeds (days) | Behavioral Assay (days) | Mice |
|---|---|---|---|---|---|---|---|---|---|
| D1 | KLH (vehicle) | 50 μg KLH | 1 | 50 μg dSRNA | s.c./s.c./s.c. | 0, 14, 28 | 38 | 42 | 4 |
| D2 | H-TT-Alum-RNA(L) | 50 μg Her-TT | 1 | 10 μg dSRNA | s.c./s.c./s.c. | 0, 14, 28 | 38 | 42 | 4 |
| D3 | H-TT-Alum-RNA(M) | 50 μg Her-TT | 1 | 25 μg dSRNA | s.c./s.c./s.c. | 0, 14, 28 | 38 | 42 | 4 |
| D4 | H-TT-Alum-RNA(H) | 50 μg Her-TT | 1 | 50 μg dSRNA | s.c./s.c./s.c. | 0, 14, 28 | 38 | 42 | 4 |
| D5 | KLH (vehicle) | 50 μg KLH | 0.2 | 50 μg dSRNA | s.c./s.c./s.c. | 0, 14, 28 | 38 | 42 | 4 |
| D6 | H-TT-Alum(L)-RNA | 50 μg Her-TT | 0.2 | 50 μg dSRNA | s.c./s.c./s.c. | 0, 14, 28 | 38 | 42 | 4 |
| D7 | H-TT-Alum(M)-RNA | 50 μg Her-TT | 0.5 | 50 μg dSRNA | s.c./s.c./s.c. | 0, 14, 28 | 38 | 42 | 4 |
| D8 | H-TT-Alum(H)-RNA | 50 μg Her-TT | 1 | 50 μg dSRNA | s.c./s.c./s.c. | 0, 14, 28 | 38 | 42 | 4 |

TABLE S3

Series E: Dosing alum with CpG study design

| Group | Vaccine | HerTT (μg/dose) | Alum (mg/mL) | Adjuvant | Route | Vaccination Schedule (days) | Bleeds (days) | Behavioral Assay (days) | Mice |
|---|---|---|---|---|---|---|---|---|---|
| E1 | KLH (vehicle) | 50 μg KLH | 0.5 | 50 μg CpG | s.c./s.c./s.c | 0, 14, 28 | 38 | 42 | 4 |
| E2 | H-TT-Alum(L)-CpG | 50 μg Her-TT | 0.2 | 50 μg CpG | s.c./s.c./s.c | 0, 14, 28 | 38 | 42 | 4 |
| E3 | H-TT-Alum(M)-CpG | 50 μg Her-TT | 0.5 | 50 μg CpG | s.c./s.c./s.c | 0, 14, 28 | 38 | 42 | 4 |
| E4 | H-TT-Alum(H)-CpG | 50 μg Her-TT | 1 | 50 μg CpG | s.c./s.c./s.c | 0, 14, 28 | 38 | 42 | 4 |

TABLE S4

Series F: dsRNA as an adjuvant for stability studies and using liposomes

| Group | Vaccine | HerTT (μg/dose) | Alum (mg/mL) | Adjuvant | Route | Vaccination Schedule (days) | Bleeds (days) | Behavioral Assay (days) | Mice |
|---|---|---|---|---|---|---|---|---|---|
| F1 | H-TT-Alum-RNA (1 d) (25% trehalose, w/v) | 50 μg Her-TT | 0.2 | 50 μg dSRNA | s.c./s.c./s.c. | 0, 14, 28 | 38 | 42 | 5 |
| F2 | H-TT-Alum-RNA (30 d) (25% trehalose, w/v) | 50 μg Her-TT | 0.2 | 50 μg dSRNA | s.c./s.c./s.c. | 0, 14, 28 | 38 | 42 | 5 |
| F3 | H-TT-Alum-RNA-Lyo (25% trehalose, w/v) | 50 μg Her-TT | 0.2 | 50 μg dSRNA | s.c./s.c./s.c. | 0, 14, 28 | 38 | 42 | 5 |
| F4 | H-TT-Alum-RNA-Lyo (30 d) (25% trehalose, w/v) | 50 μg Her-TT | 0.2 | 50 μg dSRNA | s.c./s.c./s.c. | 0, 14, 28 | 38 | 42 | 5 |

TABLE S5

Series G: Stability studies with CpG under lyophilized and liquid conditions

| Group | Vaccine | HerTT (μg/dose) | Alum (mg/mL) | Adjuvant | Route | Vaccination Schedule (days) | Bleeds (days) | Behavioral Assay (days) | Mice |
|---|---|---|---|---|---|---|---|---|---|
| G1 | H-TT-Alum-CpG (1 d, 4° C.) (>5% trehalose, w/v) | 50 μg KLH | 1 | 50 μg CpG | s.c./s.c./s.c. | 0, 14, 28 | 38 | 42 | 5 |
| G2 | H-TT-Alum-CpG (30 d, 4° C.) (>5% trehalose, w/v) | 50 μg Her-TT | 1 | 50 μg CpG | s.c./s.c./s.c. | 0, 14, 28 | 38 | 42 | 5 |
| G3 | H-TT-Alum-CpG-Lyo (>5% trehalose, w/v) | 50 μg Her-TT | 1 | 50 μg CpG | s.c./s.c./s.c. | 0, 14, 28 | 38 | 42 | 5 |
| G4 | H-TT-Alum-CpG-Lyo (30 d) (>5% trehalose, w/v) | 50 μg Her-TT | 1 | 50 μg CpG | s.c./s.c./s.c. | 0, 14, 28 | 38 | 42 | 5 |
| G5 | H-TT-Alum-CpG (0 d) (25% trehalose, w/v) | 50 μg Her-TT | 1 | 50 μg CpG | s.c /s.c./s.c. | 0, 14, 28 | 38 | 42 | 5 |
| G6 | H-TT-Alum-CpG (30 d, RT) (25% trehalose, w/v) | 50 μg Her-TT | 1 | 50 μg CpG | s.c./s.c./s.c. | 0, 14, 28 | 38 | 42 | 5 |
| G7 | H-TT-Alum-CpG-Lyo (25% trehalose, w/v) | 50 μg Her-TT | 1 | 50 μg CpG | s.c./s.c./s.c. | 0, 14, 28 | 38 | 42 | 5 |
| G8 | H-TT-Alum-CpG-Lyo (30 d) (25% trehalose, w/v) | 50 μg Her-TT | 1 | 50 μg CpG | s.c./s.c./s.c. | 0, 14, 28 | 38 | 42 | 5 |

DOCUMENTS CITED

1. Rudd RA; Seth P; David F; L, S. Increases in Drug and Opioid-Involved Overdose Deaths—United States, 2010-2015. *MMWR Morb Mortal Wkly Rep* 2016, 65, 1445-1452.
2. Miller, M.; Barber, C. W.; Leatherman, S.; et al. Prescription opioid duration of action and the risk of unintentional overdose among patients receiving opioid therapy. *JAMA Internal Medicine* 2015, 175, (4), 608-615.
3. Mars, S. G.; Bourgois, P.; Karandinos, G.; Montero, F.; Ciccarone, D. "Every 'never' I ever said came true": transitions from opioid pills to heroin injecting. *Int J Drug Policy* 2014, 25, (2), 257-66.
4. Pollini, R. A.; Banta-Green, C. J.; Cuevas-Mota, J.; Metzner, M.; Teshale, E.; Garfein, R. S. Problematic use of prescription-type opioids prior to heroin use among young heroin injectors. *Substance Abuse and Rehabilitation* 2011, 2, 173-180.
5. Principles of Drug Addiction Treatment: A Research-Based Guide, Third Edition. *NIH National Institute on Drug Abuse; U.S. Department of Health and Human Services* 2012.
6. Hoogsteder, P. H. J.; Kotz, D.; van Spiegel, P. I.; Viechtbauer, W.; van Schayck, O. C. P. Efficacy of the nicotine vaccine 3'-AmNic-rEPA (NicVAX) co-administered with varenicline and counselling for smoking cessation: a randomized placebo-controlled trial. *Addiction* 2014, 109, (8), 1252-1259.
7. Hieda, Y.; Keyler, D. E.; Ennifar, S.; Fattom, A.; Pentel, P. R. Vaccination against nicotine during continued nicotine administration in rats: immunogenicity of the vaccine and effects on nicotine distribution to brain. *International Journal of Immunopharmacology* 2000, 22, (10), 809-819.

8. Kimishima, A.; Wenthur, C. J.; Eubanks, L. M.; Sato, S.; Janda, K. D. Cocaine Vaccine Development: Evaluation of Carrier and Adjuvant Combinations That Activate Multiple Toll-Like Receptors. *Mol Pharm* 2016, 13, (11), 3884-3890.

9. Orson, F. M.; Wang, R.; Brimijoin, S.; Kinsey, B. M.; Singh, R. A.; Ramakrishnan, M.; Wang, H. Y.; Kosten, T. R. The future potential for cocaine vaccines. *Expert Opin Biol Ther* 2014, 14, (9), 1271-83.

10. Miller, M. L.; Moreno, A. Y.; Aarde, S. M.; Creehan, K. M.; Vandewater, S. A.; Vaillancourt, B. D.; Wright, M. J.; Janda, K. D.; Taffe, M. A. A methamphetamine vaccine attenuates methamphetamine-induced disruptions in thermoregulation and activity in rats. *Biological psychiatry* 2013, 73, (8), 721-728.

11. Gooyit, M.; Miranda, P. O.; Wenthur, C. J.; Ducime, A.; Janda, K. D. Influencing Antibody-Mediated Attenuation of Methamphetamine CNS Distribution through Vaccine Linker Design. *ACS Chem Neurosci* 2016.

12. Stowe, G. N.; Vendruscolo, L. F.; Edwards, S.; Schlosburg, J. E.; Misra, K. K.; Schulteis, G.; Mayorov, A. V.; Zakhari, J. S.; Koob, G. F.; Janda, K. D. A vaccine strategy that induces protective immunity against heroin. *J Med Chem* 2011, 54, (14), 5195-204.

13. Bremer, P. T.; Schlosburg, J. E.; Lively, J. M.; Janda, K. D. Injection route and TLR9 agonist addition significantly impact heroin vaccine efficacy. *Mol Pharm* 2014, 11, (3), 1075-80.

14. Bonese, K. F.; Wainer, B. H.; Fitch, F. W.; Rothberg, R. M.; Schuster, C. R. Changes in heroin self-administration by a rhesus monkey after morphine immunisation. *Nature* 1974, 252, (5485), 708-710.

15. Anton, B.; Salazar, A.; Florez, A.; Matus, M.; Marin, R.; Hernandez, J.-A. Vaccines against morphine/heroine and its use as effective medication for preventing relapse to opiate addictive behaviors. *Human vaccines* 2009, 5, (4), 214-229.

16. Aguilar, J. C.; Rodriguez, E. G. Vaccine adjuvants revisited. *Vaccine* 2007, 25, (19), 3752-62.

17. Verthelyi, D.; Ishii, K. J.; Gursel, M.; Takeshita, F.; Klinman, D. M. Human Peripheral Blood Cells Differentially Recognize and Respond to Two Distinct CpG Motifs. *The Journal of Immunology* 2001, 166, (4), 2372-2377.

18. Hartmann, G.; Krieg, A. M. Mechanism and Function of a Newly Identified CpG DNA Motif in Human Primary B Cells. *The Journal of Immunology* 2000, 164, (2), 944-953.

19. Bremer, P. T.; Schlosburg, J. E.; Banks, M. L.; Steele, F. F.; Zhou, B.; Poklis, J. L.; Janda, K. D. Development of a Clinically-Viable Heroin Vaccine. *Journal of the American Chemical Society* 2017.

20. Stahl-Hennig, C.; Eisenblatter, M.; Jasny, E.; Rzehak, T.; Tenner-Racz, K.; Trumpfheller, C.; Salazar, A. M.; Uberla, K.; Nieto, K.; Kleinschmidt, J.; Schulte, R.; Gissmann, L.; Muller, M.; Sacher, A.; Racz, P.; Steinman, R. M.; Uguccioni, M.; Ignatius, R. Synthetic double-stranded RNAs are adjuvants for the induction of T helper 1 and humoral immune responses to human papillomavirus in rhesus macaques. *PLoS Pathog* 2009, 5, (4), e1000373.

21. Lee, S.; Nguyen, M. T. Recent advances of vaccine adjuvants for infectious diseases. *Immune Netw* 2015, 15, (2), 51-7.

22. Peine, K. J.; Bachelder, E. M.; Vangundy, Z.; Papenfuss, T.; Brackman, D. J.; Gallovic, M. D.; Schully, K.; Pesce, J.; Keane-Myers, A.; Ainslie, K. M. Efficient delivery of the toll-like receptor agonists polyinosinic:polycytidylic acid and CpG to macrophages by acetalated dextran microparticles. *Mol Pharm* 2013, 10, (8), 2849-57.

23. Wickner, R. B. Double-stranded RNA viruses of *Saccharomyces cerevisiae*. *Microbiological Reviews* 1996, 60, (1), 250-265.

24. <J. Virol.—2014-Claudepierre-5242-55.pdf>.

25. Lockner, J. W.; Ho, S. O.; McCague, K. C.; Chiang, S. M.; Do, T. Q.; Fujii, G.; Janda, K. D. Enhancing nicotine vaccine immunogenicity with liposomes. *Bioorg Med Chem Lett* 2013, 23, (4), 975-8.

26. Schlosburg, J. E.; Vendruscolo, L. F.; Bremer, P. T.; Lockner, J. W.; Wade, C. L.; Nunes, A. A. K.; Stowe, G. N.; Edwards, S.; Janda, K. D.; Koob, G. F. Dynamic vaccine blocks relapse to compulsive intake of heroin. *Proceedings of the National Academy of Sciences* 2013, 110, (22), 9036-9041.

27. Bremer, P. T.; Janda, K. D. Investigating the effects of a hydrolytically stable hapten and a Th1 adjuvant on heroin vaccine performance. *J Med Chem* 2012, 55, (23), 10776-80.

28. Gottas, A.; Boix, F.; Oiestad, E. L.; Vindenes, V.; Morland, J. Role of 6-monoacetylmorphine in the acute release of striatal dopamine induced by intravenous heroin. *Int J Neuropsychopharmacol* 2014, 17, (9), 1357-65.

29. Kamendulis, L. M.; Brzezinski, M. R.; Pindel, E. V.; Bosron, W. F.; Dean, R. A. Metabolism of cocaine and heroin is catalyzed by the same human liver carboxylesterases. *Journal of Pharmacology and Experimental Therapeutics* 1996, 279, (2), 713-717.

30. Bremer, P. T.; Kimishima, A.; Schlosburg, J. E.; Zhou, B.; Collins, K. C.; Janda, K. D. Combatting Synthetic Designer Opioids: A Conjugate Vaccine Ablates Lethal Doses of Fentanyl Class Drugs. *Angew Chem Int Ed Engl* 2016, 55, (11), 3772-5.

31. Noe, S. M.; Green, M. A.; HogenEsch, H.; Hem, S. L. Mechanism of immunopotentiation by aluminum-containing adjuvants elucidated by the relationship between antigen retention at the inoculation site and the immune response. *Vaccine* 2010, 28, (20), 3588-94.

32. Kool, M.; Fierens, K.; Lambrecht, B. N. Alum adjuvant: some of the tricks of the oldest adjuvant. *J Med Microbiol* 2012, 61, (Pt 7), 927-34.

33. Clapp, T.; Siebert, P.; Chen, D.; Jones Braun, L. Vaccines with aluminum-containing adjuvants: optimizing vaccine efficacy and thermal stability. *J Pharm Sci* 2011, 100, (2), 388-401.

34. Clausi, A. L.; Merkley, S. A.; Carpenter, J. F.; Randolph, T. W. Inhibition of aggregation of aluminum hydroxide adjuvant during freezing and drying. *J Pharm Sci* 2008, 97, (6), 2049-61.

35. Smallshaw, J. E.; Vitetta, E. S. A lyophilized formulation of RiVax, a recombinant ricin subunit vaccine, retains immunogenicity. *Vaccine* 2010, 28, (12), 2428-35.

36. Lee, S. B.; Crouse, C. A.; Kline, M. C. Optimizing Storage and Handling of DNA Extracts. *Forensic Sci Rev* 2010, 22, (2), 131-44.

37. Méndez, I. Z. R.; Shi, Y.; HogenEsch, H.; Hem, S. L. Potentiation of the immune response to non-adsorbed antigens by aluminum-containing adjuvants. *Vaccine* 2007, 25, (5), 825-833.

All patents and publications referred to herein are incorporated by reference herein to the same extent as if each individual publication was specifically and individually indicated to be incorporated by reference in its entirety.

STATEMENTS OF THE INVENTION

In various embodiments, the invention can provide a composition for immunization of a mammal to produce an anti-heroin antibody, comprising:
a conjugate of a hapten of formula 7

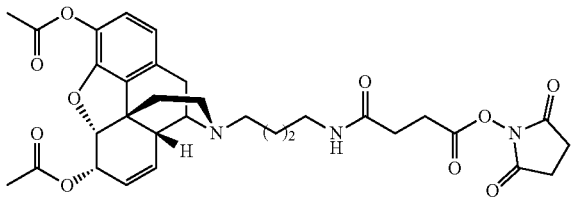

7 and a carrier protein; and,
an adjuvant comprising a TLR9 agonist, or a TLR3 agonist, in aqueous solvent. For example, the carrier protein can be tetanus toxoid (TT). In other embodiments, the carrier protein can be a mutant diphtheria toxoid termed CRM.

For example, the TLR9 agonist can be CpG. CpG oligodeoxynucleotide 1826 is a B-class ODN that stimulates B-cell responses though TLR9 and was recently shown to elicit robust titers in anti-heroin vaccine studies. In other embodiments the TSR3 agonist can be a natural or synthetic dsRNA, e.g., polyinosiic:polycytidylicacid (poly 1:C), a molecular pattern associated with viral replication, which elicits an immune response via TLR3 and has been used as an effective adjuvant in several vaccine studies.

In various embodiments, the composition can further comprise alum as an adjuvant. In other embodiments, the composition can further comprise conjugatable adjuvant lipid vesicles (CALV) as an alternative vehicle for vaccine delivery.

It has been surprisingly discovered that the composition further comprising trehalose as a cryoprotectant possesses a marked resistance to degradation on storage, particularly as a dry, lyophilized form. The lyophilized form of the immunogenic composition has been found to be stable on storage at room temperature to such a degree that the composition exhibits no decrease in eliciting production of anti-heroin antibodies over that period of time. This is advantageous from the perspective of composition storage in clinics where heroin overdoses or heroin addiction is being treated by physicians.

Inspection of Table 1, above, shows that compositions comprising trehalose, such as 25% trehalose (see samples G5-G8) possess no loss of potency at the starting point due to the presence of trehalose, and retain a significantly higher degree of potency on storage, being without detectable degradation or loss of immunogenic capacity at 30 days storage, in comparison to samples E2-E4 (no cryopreservative). Storage stability of the dry lyophilized form is particularly notable. Potency is indicated by a higher dosage of heroin required to produce a specific degree of antinociceptive bioactivity in the hot plate and tail flick tests of the antinociception assay.

Accordingly, a preferred composition is the conjugate of the hapten of formula 7 with carrier protein tetanus toxoid (TT) further comprising CpG, alum, and trehalose. A solid lyophilized form of the composition can be stored at room temperature at least thirty days without loss of potency. Trehalose is also effective as a cryoprotectant in other compositions.

In various embodiments, the invention can provide a method of raising an anti-heroin antibody in a patient, comprising administering an effective amount of the composition of the invention to the patient. The anti-heroin antibody raised thereby can be an effective treatment of a heroin overdose in the patient, reducing the heroin titer in the patient's bloodstream sufficiently to reduce the amount of heroin acting in the patient's nervous system.

The invention can also provide a treatment for heroin addiction in a patient, wherein the anti-heroin antibody is raised in the patient as an effective treatment for heroin addiction blocking the effects of the drug. Due to the low cross-reactivity of the antibodies formed by administration of the immunogenic composition of the invention, the anti-heroin antibody does not significantly cross-react with opioids other than 6-acetylmorphine. This is notable in that the treatment program for heroin addiction may involve the administration of other opioids, which retain their effectiveness in the presence of the antibodies raised by administration of a composition of the present invention.

EXAMPLES

Abbreviations: OPR, opioid pain reliever; 6-AM, 6-monoacetylmorphine; PAMPS, pathogen-associated molecular patterns; LPS, lipopolysaccharides; CpG ODN, cytosine-phosphodiester-guanine oligodeoxynucleotide; dsRNA, double-stranded RNA; TLR, Toll-like receptor; TT, tetanus toxoid; CRM, non-toxic mutant of diphtheria toxin; KLH, keyhole limpet hemocyanin; PBS, phosphate buffered saline; EDC, 1-ethyl-3-(3-dimethylaminopropyl)carbodiimide; MALDI-ToF MS, matrix-assisted laser desorption ionization time-of-flight mass spectrometry; CALV, conjugatable adjuvant lipid vesicles; s.c., subcutaneous; SPR, surface plasmon resonance; Lyo, lyophilized.

Materials and Methods $^1$H and $^{13}$C NMR spectra were obtained on Bruker spectrometers. Multiplicities are quoted as singlet (s), doublet (d), triplet (t), unresolved multiplet (m), or broad signal (br). All chemical shifts are given on the δ-scale in parts per million ((ppm) relative to internal CDCl$_3$ (b 7.26, $^1$H NMR; δ 77.0, $^{13}$C NMR). $^1$H coupling constants (J values) are given in Hz. The concentration of the NMR samples was in the range of 2-5 mg/mL. Analytical LCMS was performed on an Agilent ESI-ToF (LC/MSD ToF) with an Agilent Zorbax 300SB-C$_8$ (4.6×50 mm) 5 µm column using a flow rate of 0.5 mL/min. The LCMS was run using the following solvents: Solvent A: 0.1% formic acid, Solvent B: 0.1% formic acid in acetonitrile (MeCN) and each run was ten minutes (0-7 min: 5-95% Solvent B, 7-10 min: 95% Solvent B) with detection at wavelength 254 nm. Matrix-assisted laser desorption/ionization (MALDI) mass spectra were obtained using an Applied Biosystems Voyager DE.

All chemicals were purchased from commercial sources, with the exception of heroin, which was obtained from NIDA, and used without further purification. Sodium triacetoxyborohydride (NaBH(OAc)$_3$), 1-[Bis(dimethylamino) methylene]-1H-1,2,3-triazolo[4,5-b]pyridinium 3-oxid hexafluorophosphate (HATU), α-chloroethylchloroformate (ACE-Cl), N-hydroxysuccinimide (NHS), and bovine serum albumin (BSA) were purchased from Sigma. Mono-t-butyl succinate was purchased from Combi-Blocks, Inc. Tetanus toxoid (TT) was purchased from UMass Biologics and mutant nontoxic form of diphtheria toxin (CRM197) was purchased from Fina Biosolutions. N-Boc-b-aminobutanal 3 was synthesized according to literature procedure.[1] All reactions were run under inert gas and with dry, distilled solvents unless otherwise noted. The previously mentioned, LCMS as well as TLC visualized with UV light and ninhydrin staining were routinely used to monitor reactions. All exact masses were computed for the following isotopic compositions: $^{1}$H, $^{12}$C, $^{14}$N, and $^{16}$O.

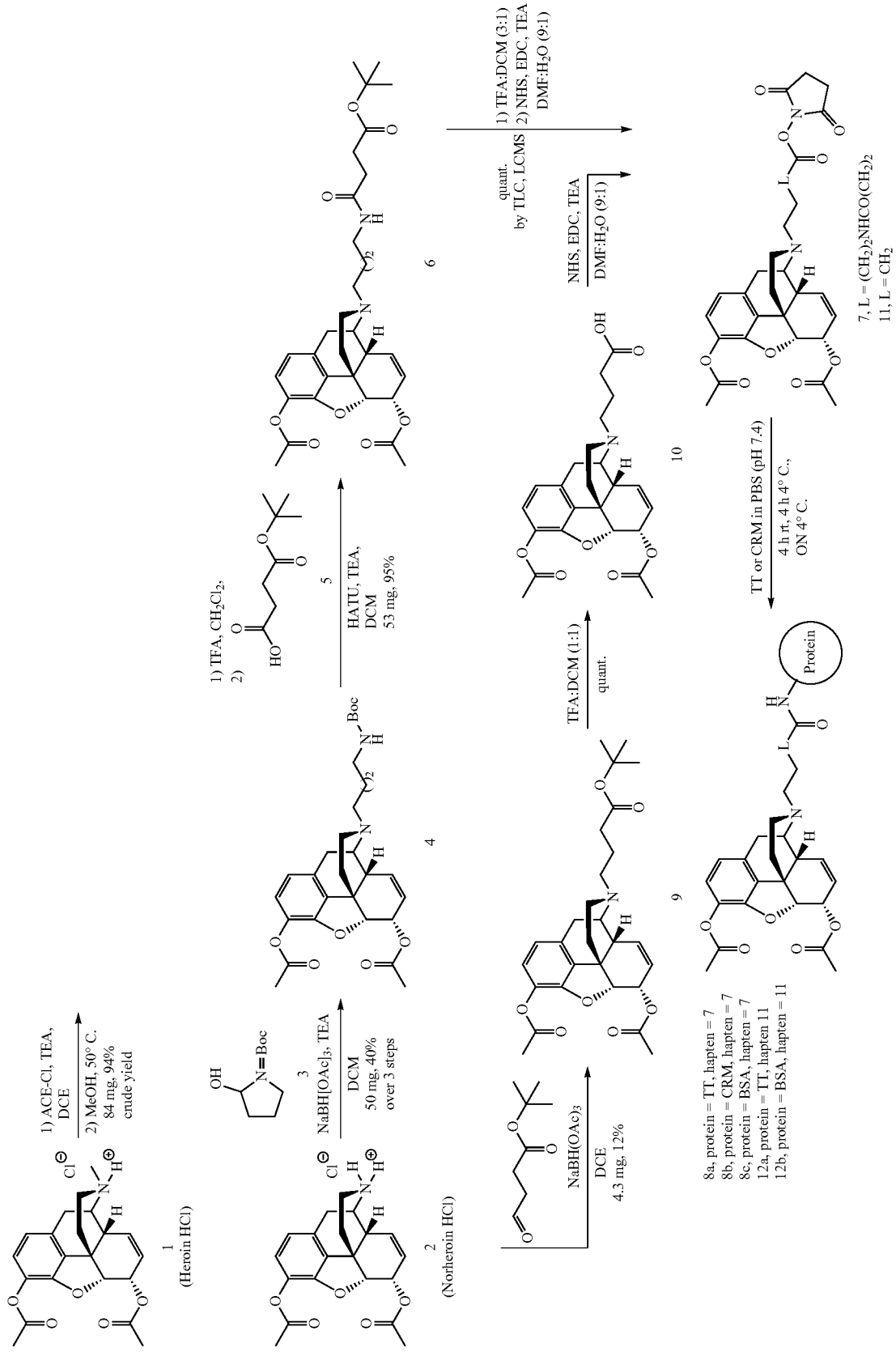
Scheme 1. Synthesis of heroin haptens and conjugation to carrier proteins

(4aR,7S,7aR,12bS)-3-(4-((tert-butoxycarbonyl)amino)butyl)-2,3,4,4a,7,7a-hexahydro-1H-4,12-methanobenzofuro[3,2-e]isoquinoline-7,9-diyl diacetate (4)

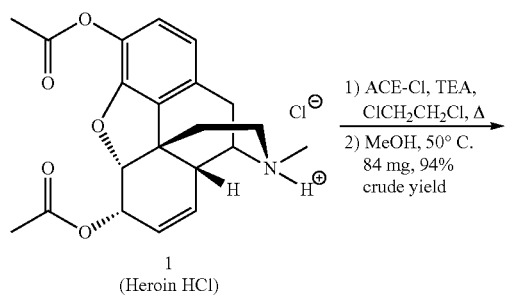

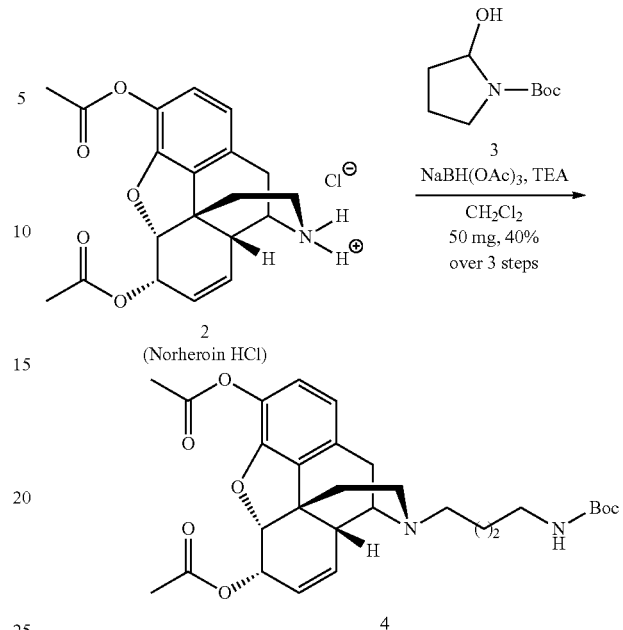

To a solution of heroin hydrochloride (100 mg, 0.25 mmol) in 4 mL of dry, 1,2-dichloroethane was added N,N-diisopropylethylamine (343 µL, 2.0 mmol, 8 equiv) and ACE-Cl (216 µL, 2.0 mmol, 8 equiv) at rt. The solution was then heated to reflux for 4 h under argon with monitoring by TLC (9:1 CH$_2$Cl$_2$:MeOH). The reaction solution was then cooled and the solvent was removed under reduced pressure. The residue was then dissolved in 10 mL CH$_2$Cl$_2$ and washed with saturated bicarbonate (2×10 mL). The aqueous layers were combined and washed with EtOAc (1×10 mL). The organic layers were combined and dried with sodium sulfate (Na$_2$SO$_4$) and the solution was filtered and solvents were removed. The residue was then dissolved in a portion of MeOH, stirred at 50° C. for 12 minutes and monitored by TLC. Hydrolysis of the carbamate with MeOH must be carefully monitored, as deacetylation of norheroin may occur with proloned heating. The solvents were evaporated and the product 2 (84 mg, 94% crude yield) was used in the next step as obtained. ESI-MS: MS (m/z): calcd for C$_{20}$H$_{22}$NO$_5$$^+$: 356.2, found: 356.2 [M+H]$^+$.

Crude norheroin 2 (84 mg, 0.24 mmol) was dissolved in 4 mL of dry 1,2-dichloroethane, followed by addition of 3 (88 mg, 0.48 mmol, 2 equiv)[1], triethylamine (66 µL, 0.48 mmol, 2 equiv), and NaBH(OAc)$_3$ (150 mg, 0.72 mmol, 3 equiv). The reaction solution was allowed to stir for 4 h and was monitored by TLC. The reaction was quenched with water and washed with saturated sodium bicarbonate (2×10 mL). The organic layer was dried with Na$_2$SO$_4$ and solvents were evaporated. The residue was purified by flash chromatography using 5% MeOH in EtOAc. The fractions were collected and the solvents were evaporated to give 50 mg of 4 (40% yield over three steps). NMR spectra were consistent with literature values.[2] $^1$H NMR (500 MHz, CDCl$_3$) δ 6.75 (d, J=8.1 Hz, 1H), 6.56 (d, J=8.2 Hz, 1H), 5.61 (dt, J=10.0, 2.5 Hz, 1H), 5.41 (dt, J=10.1, 2.5 Hz, 1H), 5.24 (s, 1H), 5.14 (d, J=2.7 Hz, 1H), 5.10 (d, J=6.6 Hz, 1H), 3.43 (dd, J=6.0, 3.2 Hz, 1H), 3.17-3.11 (m, 2H), 2.98 (d, J=18.7 Hz, 1H), 2.77 (s, 1H), 2.67 (dd, J=12.6, 4.6 Hz, 1H), 2.53 (q, J=6.1 Hz, 2H), 2.35 (d, J=6.0 Hz, 1H), 2.32 (s, 1H), 2.26 (s, 3H), 2.12 (s, 3H), 2.03 (s, 1H), 1.87 (d, J=13.0 Hz, 1H), 1.56 (q, J=6.9 Hz, 4H), 1.43 (s, 9H). $^{13}$C NMR (126 MHz, CDCl$_3$) δ 170.40, 168.40, 156.04, 149.32, 132.12, 131.74, 131.50, 129.52, 128.41, 121.88, 119.28, 88.67, 78.94, 68.06, 56.98, 54.33, 44.59, 43.31, 40.45, 40.35, 34.94, 28.46, 27.81, 24.88, 21.57, 20.63, 20.60. ESI-MS: MS (m/z): calcd for C$_{29}$H$_{39}$N$_2$O$_7$$^+$: 527.3, found: 527.3 [M+H]$^+$.

(4aR,7S,7aR,12bS)-3-(4-(4-(tert-butoxy)-4-oxobutanamido)butyl)-2,3,4,4a,7,7a-hexahydro-1H-4,12-methanobenzofuro[3,2-e]isoquinoline-7,9-diyl diacetate (6)

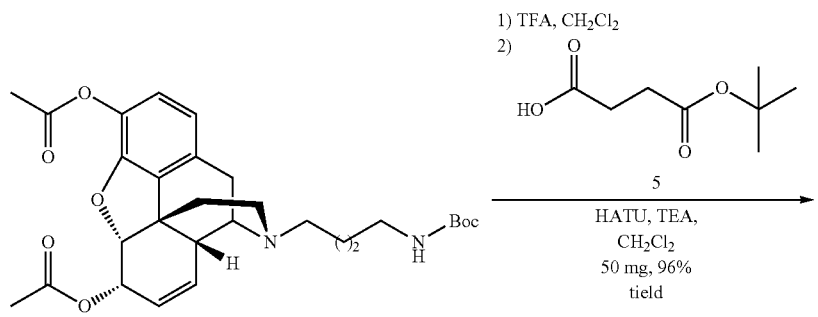

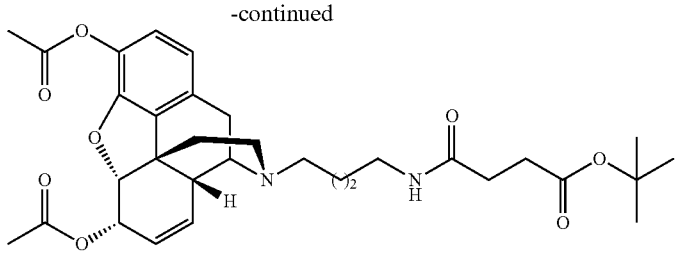

6

Compound 4 (50 mg, 0.09 mmol) was deprotected using 2 mL of a 1:1 solution of TFA and $CH_2Cl_2$. The deprotection was allowed to stir for 2 h, and was monitored by TLC (9:1 $CH_2Cl_2$:MeOH) and LC-MS. ESI-MS: MS (m/z): calcd for $C_{24}H_{31}N_2O_5^+$: 427.2, found: 427.2 $[M+H]^+$. After complete deprotection of the Boc group, the solvents were coevaporated with several portions of toluene and $CH_2Cl_2$. The compound was then dissolved in 1 mL of dry $CH_2Cl_2$ and 43 μL of TEA (0.31 mmol, 31 mg, 3.3 equiv). Mono-t-butyl succinate 5 (0.10 mmol, 17 mg, 1.1 equiv) and HATU (0.10 mmol, 38 mg, 1.1 equiv) were added in one portion to the solution. The reaction was allowed to stir for 3 h and monitored by TLC (9:1 $CH_2Cl_2$:MeOH). After complete formation of the amide (6), the reaction was diluted with 10 mL of $CH_2Cl_2$ and washed with saturated sodium bicarbonate. The organic layer was dried with $Na_2SO_4$ and the solvents were evaporated. The crude oil was purified by flash chromatography using 10% MeOH in $CH_2Cl_2$. The pure fractions were combined and solvents were evaporated to yield 53 mg of 6 (96% yield). $^1$H NMR (500 MHz, $CDCl_3$) δ 6.74 (d, J=8.2 Hz, 1H), 6.55 (d, J=8.2 Hz, 1H), 6.06 (s, 1H), 5.60 (d, J=10.0 Hz, 1H), 5.41 (d, J=2.3 Hz, 1H), 5.13 (d, J=6.6 Hz, 1H), 5.08 (d, J=6.6 Hz, 1H), 3.42 (s, 1H), 3.28-3.23 (m, 2H), 2.95 (d, J=18.7 Hz, 1H), 2.72 (s, 1H), 2.69-2.62 (m, 1H), 2.56 (t, J=6.8 Hz, 2H), 2.54-2.48 (m, 2H), 2.39 (t, J=6.8 Hz, 2H), 2.36-2.28 (m, 2H), 2.25 (s, 3H), 2.11 (s, 3H), 2.01 (td, J=12.2, 4.5 Hz, 1H), 1.86 (d, J=12.6 Hz, 1H), 1.57-1.50 (m, 4H), 1.42 (s, 9H). $^{13}$C NMR (126 MHz, $CDCl_3$) δ 172.32, 171.58, 170.40, 168.37, 149.32, 132.15, 131.68, 131.48, 129.50, 128.37, 121.83, 119.25, 88.68, 80.65, 68.08, 56.82, 54.16, 44.70, 43.32, 40.47, 39.26, 35.07, 31.31, 30.86, 28.02, 27.34, 24.82, 21.59, 20.62, 20.57. ESI-MS: MS (m/z): calcd for $C_{32}H_{43}N_2O_8^+$: 583.3, found: 583.3 $[M+H]^+$.

(4aR,7S,7aR,12bS)-3-(4-(4-((2,5-dioxopyrrolidin-1-yl)oxy)-4-oxobutanamido)butyl)-2,3,4,4a,7,7a-hexahydro-1H-4,12-methanobenzofuro[3,2-e]isoquinoline-7,9-diyl diacetate (7)

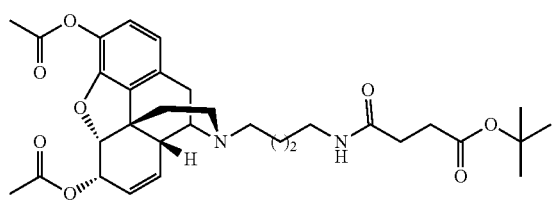

6

| quant. by TLC, LCMS | 1) TFA:$CH_2Cl_2$ (3:1)<br>2) NHS, EDC, TEA<br>DMF:$H_2O$ (9:1) |

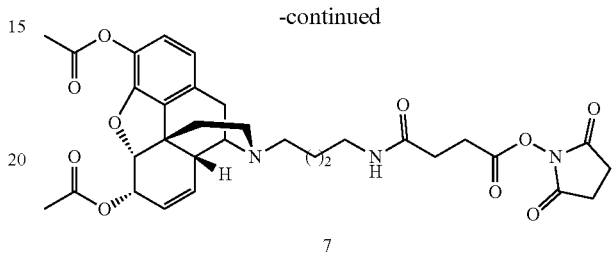

7

The t-butyl protected heroin hapten 6 was equally divided into 5 mg aliquots and was stored in the −20° C. as a solid until needed for conjugation with carrier protein. To a 5 mg aliquot of 6 (0.009 mmol) was added 1 mL of a solution of TFA and $CH_2Cl_2$ (3:1). The deprotection was allowed to proceed overnight at rt and was monitored by TLC (9:1 $CH_2Cl_2$:MeOH). The deprotected hapten was then coevaporated with several portions of toluene and $CH_2Cl_2$. The deprotected acid was dissolved in 500 uL of a 9:1 DMF:$H_2O$ solution, followed by addition of TEA (0.03 mmol, 3.8 μL, 3 equiv). NHS (0.09 mmol, 10.4 mg, 10 equiv) and N-(3-dimethylaminopropyl)-N'-ethylcarbodiimide hydrochloride (EDC, 0.09 mmol, 17.3 mg, 10 equiv) were added in one portion. The solution was allowed to stir for an hour and was monitored by LCMS. Another 5 equiv of NHS and EDC were added in one portion to the reaction. After one hour, LCMS indicated completion of the reaction. ESI-MS: MS (m/z): calcd for $C_{32}H_{38}N_3O_{10}^+$: 624.3, found: 624.2 $[M+H]^+$.

(4aR,7S,7aR,12bS)-3-(4-((2,5-dioxopyrrolidin-1-yl)oxy)-4-oxobutyl)-2,3,4,4a,7,7a-hexahydro-1H-4,12-methanobenzofuro[3,2-e]isoquinoline-7,9-diyl diacetate (11)

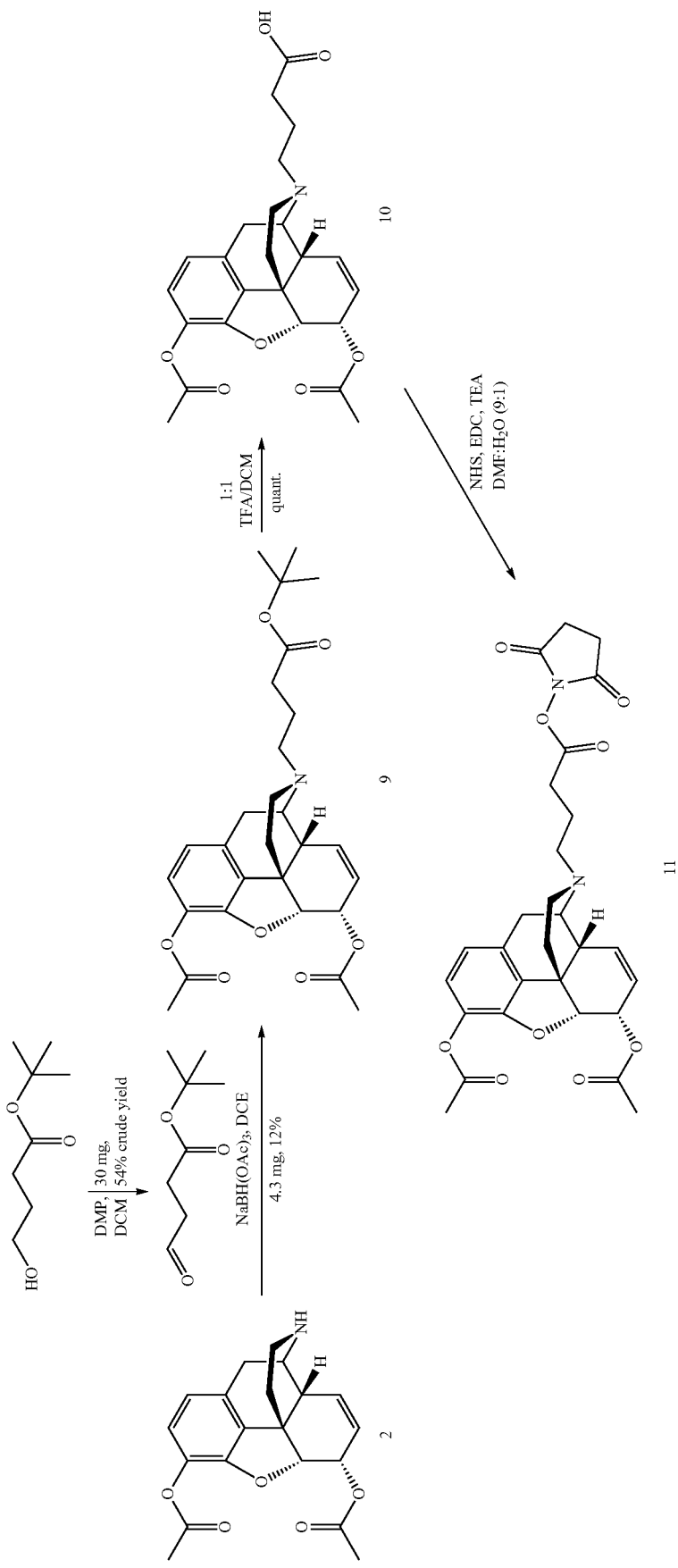

To a solution of tert-butyl 4-hydroxybutanoate (56 mg, 0.35 mmol) in 1 mL DCM was added DMP (273 mg, 0.64 mmol, 1.8 eq) and the solution was stirred for 2 h at rt. The reaction mixture was diluted with DCM and washed 3× with 10% sodium thiosulfate solution and once with saturated sodium bicarbonate solution to yield 30 mg crude tert-butyl 4-oxobutanoate (54% crude yield). Crude free-base norheroin 2 (25 mg, 0.07 mmol) was dissolved in 4 mL of dry 1,2-dichloroethane, followed by the addition of crude tert-butyl 4-oxobutanoate (30 mg, 0.19 mmol, 2.7 eq) and NaBH(OAc)$_3$ (22 mg, 0.11 mmol, 1.5 equiv). The reaction solution was allowed to stir for 2 h. The reaction mixture was diluted with DCM and washed twice with saturated sodium bicarbonate solution. Purification proceeded via preparative TLC using 5% MeOH in EtOAc as an eluent to yield 4.3 mg of 9 (12% yield). $^1$H NMR (600 MHz, CDCl$_3$) δ 6.78 (d, J=8.2 Hz, 1H), 6.59 (d, J=8.2 Hz, 1H), 5.66-5.61 (m, 1H), 5.44 (dt, J=10.0, 2.7 Hz, 1H), 5.17 (dd, J=5.9, 2.8 Hz, 1H), 5.12 (dd, J=6.6, 1.0 Hz, 1H), 3.44 (s, 1H), 2.99 (d, J=18.7 Hz, 1H), 2.78-2.73 (m, 1H), 2.68 (dd, J=12.4, 4.7 Hz, 1H), 2.55 (d, J=26.4 Hz, 1H), 2.40-2.35 (m, 2H), 2.35 (s, 1H), 2.32 (t, J=7.2 Hz, 2H), 2.29 (s, 3H), 2.16 (s, 3H), 2.08-2.00 (m, 1H), 1.89 (d, J=10.8 Hz, 1H), 1.84-1.76 (m, 2H), 1.48 (s, 9H). $^{13}$C NMR (151 MHz, CDCl$_3$) δ 173.18, 170.66, 168.62, 149.54, 131.85, 131.78, 129.86, 128.48, 121.99, 119.46, 88.96, 80.32, 68.34, 57.20, 54.19, 44.83, 43.56, 40.70, 35.33, 33.43, 28.29, 23.18, 22.03, 20.84, 20.79. HRMS (ESI-TOF): MS (m/z): calcd for C$_{28}$H$_{36}$NO$_7$ 498.2486, found: 498.2477.

Compound 9 was deprotected using 1 mL 1:1 TFA/DCM over 18 h to quantitatively afford 10 as the TFA salt. $^1$H NMR (600 MHz, CDCl$_3$) δ 6.87 (d, J=8.2 Hz, 1H), 6.68 (d, J=8.4 Hz, 1H), 5.75 (d, J=10.2 Hz, 1H), 5.42 (s, 1H), 5.22 (d, J=6.8 Hz, 1H), 5.17 (s, 1H), 4.31 (s, 1H), 3.53 (s, 1H), 3.29 (s, 2H), 3.24-3.08 (m, 2H), 2.89 (d, J=21.7 Hz, 2H), 2.52 (s, 2H), 2.28 (s, 3H), 2.12 (s, 3H), 1.25 (s, 2H). $^{13}$C NMR (151 MHz, CDCl$_3$) δ 170.77, 168.65, 149.63, 133.01, 130.89, 129.28, 127.62, 125.30, 123.84, 120.09, 87.27, 66.98, 58.79, 53.96, 46.85, 41.39, 37.83, 32.46, 30.49, 29.84, 21.73, 20.65, 20.54, 19.25. HRMS (ESI-TOF): MS (m/z): calcd for C$_{24}$H$_{28}$NO$_7$ 442.1860, found: 442.1857 [M+H]$^+$. The procedure used for the preparation of NHS ester of 7 was also used to synthesize 11.

Conjugation of activated heroin haptens 7 and 11 to carrier protein tetanus toxoid (TT), diphtheria toxin mutant (CRM) or bovine serum albumin (BSA)

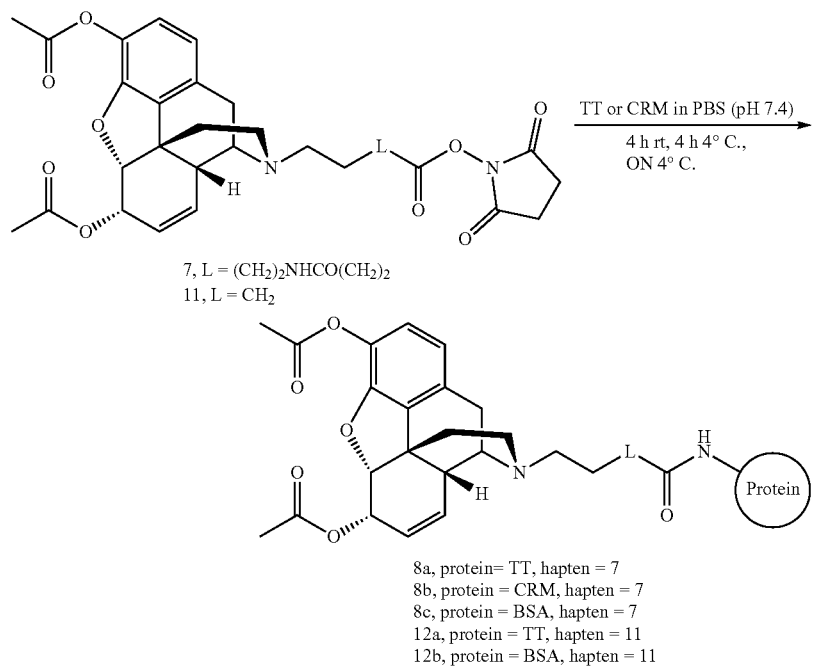

7, L = (CH$_2$)$_2$NHCO(CH$_2$)$_2$
11, L = CH$_2$ 8a, protein = TT, hapten = 7
8b, protein = CRM, hapten = 7
8c, protein = BSA, hapten = 7
12a, protein = TT, hapten = 11
12b, protein = BSA, hapten = 11

Prior to conjugation, tetanus toxoid (TT) and mutant nontoxic form of diphtheria toxin (CRM) were dialyzed against phosphate buffered solution, pH 7.4 (PBS) using Slide-A-Lyzer™ dialysis cassettes (ThermoFisher) with a 10K molecular weight cutoff. The buffer was exchanged after 2 h at rt, 4 h at 4° C. and overnight at 4° C. A portion of the reaction solution (450 μL) of 7 or 11 was added to 4.5 mg of TT or CRM (1 mg/mL in PBS buffer, pH 7.4). Another portion (50 μL) was added to 0.5 mg of bovine serum albumin (BSA, 1 mg/mL in PBS buffer pH 7.4). The activated heroin hapten was allowed to react with the carrier proteins at rt for 4 h, followed by 16 h overnight at 4° C. using gentle end-over-end mixing. The reaction solutions were then dialyzed as described above. Heroin immunoconjugates were either mixed with 50% (v/v) glycerol (total immunoconjugate volume) or trehalose (total vaccine volume, % w/v) and stored in the −80° C.

MALDI-ToF MS Analysis

Heroin conjugated to BSA or CRM was run on a desalting column and then analyzed by MALDI-ToF for the hapten: carrier protein conjugation number as a surrogate for TT or CRM and for ELISAs. In order to quantify the copy number or the number of heroin haptens (Her) on BSA and CRM, the molecular weight (MW) of conjugated BSA (Her-BSA, Figures S9-10) was compared to the MW of unconjugated BSA (BSA, Figure S8) using the following formula:

$$\text{Hapten number} = \frac{(MW_{Her-Protein} - MW_{Protein})}{(MW_{Her} - MW_{H_2O})}$$

$MW_{Her-BSA} = 75,361$ or $79,667$ Da $(8c)$; $77,827$ $(12b)$ $MW_{BSA} = 66,472$ Da $MW_{CRM} = 58,417$ Da $MW_{Her-CRM} = 64,604$ Da $MW_{Her} = 526.5$ Da or $441.5$ Da $MW_{H_2O} = 18$ Da

Hapten: protein molar ratios=
17.5 and 25.9 for 8c
12.2 for 8b
26.8 for 12b

What is claimed is:

1. A composition comprising a compound of Formula (A) and an adjuvant; wherein the compound of Formula (A) is:

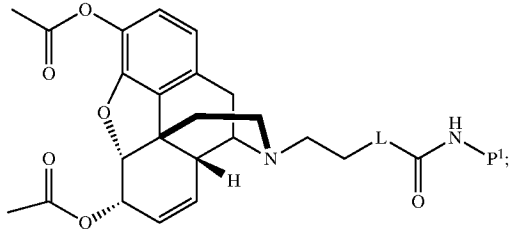

(A)

wherein:
L is —CH$_2$— or —(CH$_2$)$_2$NHCO(CH$_2$)$_2$—;
P$^1$ is a carrier protein.

2. The composition of claim 1, wherein L is —CH$_2$—.

3. The composition of claim 1, wherein the carrier protein is tetanus toxoid or mutant diphtheria toxoid.

4. The composition of claim 1, wherein the adjuvant comprises a Toll-like receptor 9 agonist or a Toll-like receptor 3 agonist.

5. The composition of claim 1, wherein the adjuvant comprises a Toll-like receptor 9 agonist, and wherein the Toll-like receptor 9 agonist is a cytosine-guanine oligodeoxynucleotide.

6. The composition of claim 5, wherein the cytosine-guanine oligodeoxynucleotide is cytosine-guanine oligodeoxynucleotide 1826.

7. The composition of claim 1, further comprising wherein the adjuvant comprises alum.

8. The composition of claim 1, wherein the adjuvant comprises a Toll-like receptor 9 agonist and alum.

9. The composition of claim 1, further comprising a cryoprotectant.

10. The composition of claim 9, wherein the cryoprotectant is trehalose.

11. The composition of claim 1, further comprising an aqueous solvent.

12. A lyophilized composition comprising a solid lyophilized form of the composition of claim 1.

13. A method of treating a heroin addiction or a heroin overdose in a patient in need thereof, the method comprising administering to the patient an effective amount of the composition of claim 1.

14. A method of raising an anti-heroin antibody in a patient in need thereof, the method comprising administering to the patient an effective amount of the composition of claim 1.

15. A compound of Formula (A):

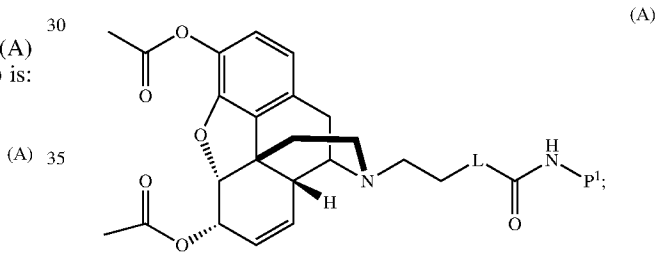

(A)

wherein:
L is —CH$_2$— or —(CH$_2$)$_2$NHCO(CH$_2$)$_2$—;
P$^1$ is a carrier protein.

16. The compound of claim 15, wherein L is —CH$_2$—.

17. The compound of claim 15, wherein the carrier protein is tetanus toxoid, mutant diphtheria toxoid, or bovine serum albumin.

18. The compound of claim 15, wherein the carrier protein is tetanus toxoid.

19. The compound of claim 1, wherein L is —(CH$_2$)$_2$NHCO(CH$_2$)$_2$—.

20. The compound of claim 15, wherein L is —(CH$_2$)$_2$NHCO(CH$_2$)$_2$—.

* * * * *